US007939253B2

(12) United States Patent
Lessnick

(10) Patent No.: US 7,939,253 B2
(45) Date of Patent: May 10, 2011

(54) METHODS AND COMPOSITIONS FOR THE DIAGNOSIS AND TREATMENT OF EWING'S SARCOMA

(75) Inventor: Stephen L. Lessnick, Salt Lake City, UT (US)

(73) Assignee: The University of Utah Research Foundation, Salt Lake City, UT (US)

(*) Notice: Subject to any disclaimer, the term of this patent is extended or adjusted under 35 U.S.C. 154(b) by 124 days.

(21) Appl. No.: 11/746,376

(22) Filed: May 9, 2007

(65) Prior Publication Data

US 2008/0280844 A1    Nov. 13, 2008

(51) Int. Cl.
*C12Q 1/68* (2006.01)
*A61K 48/00* (2006.01)

(52) U.S. Cl. .......................................... 435/6; 514/44 R
(58) Field of Classification Search ......... 435/6; 514/44
See application file for complete search history.

(56) References Cited

U.S. PATENT DOCUMENTS

2007/0078083 A1    4/2007    Barlow et al.

OTHER PUBLICATIONS

Watanabe et al., Transient up-regulation of Nkx2.2 expression in oligodendrocyte lineage cells during remyelination, Glia. 46(3):311-22, 2004.*
Pauls et al., Function and regulation of zebrafish nkx2.2a during development of pancreatic islet and ducts, Dev Biol. 304(2):875-90, 2007.*
Wang et al., Homeodomain transcription factor Nkx2.2 functions in immature cells to control enteroendocrine differentiation and is expressed in gastrointestinal neuroendocrine tumors, Endocr Relat Cancer. 2008 Nov 5. [Epub ahead of print] (one page abstract provided).*
Kim et al., Dendritic cell-tumor fusion vaccine prevents tumor growth in vivo, Biosci Biotechnol Biochem. 71(1):215-21, 2007.*
Davis et al., Ewing's sarcoma: general insights from a rare model, Cancer Cell, 9(5):331-2, 1996.*
Wang et al., Homeodomain transcription factor Nkx2.2 functions in immature cells to control enteroendocrine differentiation and is expressed in gastrointestinal neuroendocrine tumors, Endocr Relat Cancer. 16(1):267-79, 2009.*
Baird et al., Gene expression profiling of human sarcomas: insights into sarcoma biology, Cancer Res. 65(20):9226-35, 2005.*
International Search Report from PCT/US2007/068880 dated Nov. 7, 2007.
Ambros, I. M., Ambros, P. F., Strehl, S., Kovar, H., Gadner, H., and Salzer-Kuntschik, M. (1991). MIC2 is a specific marker for Ewing's sarcoma and peripheral primitive neuroectodermal tumors. Evidence for a common histogenesis of Ewing's sarcoma and peripheral primitive neuroectodermal tumors from MIC2 expression and specific chromosome aberration. Cancer 67, 1886-1893.
Arvand, A., Bastians, H., Welford, S. M., Thompson, A. D., Ruderman, J. V., and Denny, C. T. (1998). EWS/FLI1 up regulates mE2-C, a cyclin-selective ubiquitin conjugating enzyme involve'd in cyclin B destruction. Oncogene 17, 2039-2045.
Arvand, A., Welford, S. M., Teitell, M. A., and Denny, C. T. (2001). The COOH-terminal domain of FLI-1 is necessary for full tumorigenesis and transcriptional modulation by EWS/FLI-1. Cancer Res 61, 5311-5317.
Bailly, R. A., Bosselut, R., Zucman, J., Cormier, F., Delattre, O., Roussel, M., Thomas, G., and Ghysdael, J. (1994). DNA-binding and transcriptional activation properties of the EWS-FLI-1 fusion protein resulting from the t(11;22) translocation in Ewing sarcoma. Mol Cell Biol 14, 3230-3241.
Baird, K., Davis, S., Antonescu, C. R., Harper, U. L., Walker, R. L., Chen, Y., Glatfelter, A. A., Duray, P. H., and Meltzer, P.S. (2005). Gene expression profiling of human sarcomas: insights into sarcoma biology, Cancer Res 65, 9226-9235.
Braun, B. S., Frieden, R., Lessnick, S. L., May, W. A., and Denny, C. T. (1995). Identification of target genes for the Ewing's sarcoma EWS/FLI fusion protein by representational difference analysis. Mol Cell Biol 15, 4623-4630.
Briscoe, J., Sussel, L., Serup, P., Hartigan-O'Connor, D., Jessell, T. M., Rubenstein, J. L., and Ericson, J. (1999). Homeobox gene Nkx2.2 and specification of neuronal identity by graded Sonic hedgehog signaling. Nature 398, 622-627.
Cavenzzana, A. O., Miser, J. S., Jefferson, J., and Triche, T. J. (1987). Experimental evidence for a neural origin of Ewing's sarcoma of bone. Am J Pathol 127, 507-518.
Collini, P., Mezzelani, A., Modena, P., Dagrada, P., Tamborini, E., Luksch, R., Gronchi, A., Navarria, P., Sozzi, G., and Pilotti, S. (2003), Evidence of neural differentiation in a case of post-therapy primitive neuroectodermal tumor/Ewing sarcoma of bone. AM J Surg Pathol 27, 1161-1166.
Dauphinot, L., De Oliveira, C., Melot, T., Sevenet, N., Thomas, V., Weissman, B. E., and Delattre, O. (2001). Analysis of the expression of the expression of cell regulators in Ewing cell lines: EWS-FLI-1 modulates p57KIP2 and c-Myc expression. Oncogene 20, 3258-3265.
Dellatre, O., Zucman, J., Plougastel, B., Desmaze, C., Melot, T., Peter, M., Heinrich, K., Houbert, I., de Jong, P., Rouleau, G., et al. (1992). Gene fusion with an ETS DNA-binding domain caused by chromosome translocation in human tumors. Nature 359, 162-165.
Deneen, B., and Denny, C. T. (2001). Loss of p16 pathways stabilizes EWS/FLI1 expression and complements EWS/FLI1 mediated transformation. Oncogene 20, 6731-6741.
Deneen, B., Hamidi, H., and Denny, C. T. (2003). Functional analysis of the EWS/ETS target gene uridine phosphorylase. Cancer res 63, 4268-4274.
Fukuma, M., Okita, H., Hata, J., and Umezawa, A. (2003). Upregulation of Id2, an oncogenic helix-loop-helix protein, is mediates by the chimeric EWS/ets protein in Ewing sarcoma. Oncogene 22, 1-9.

(Continued)

*Primary Examiner* — Wu-Cheng Winston Shen
(74) *Attorney, Agent, or Firm* — Foley & Lardner LLP

(57) ABSTRACT

The present invention relates to methods and compositions for the detection and treatment of Ewing's sarcoma. In particular, the methods of detection relate to measuring in Ewing's sarcoma cells the expression of the NKX2.2 gene, as well as targets genes downstream of NKX2.2. The compositions and method of treatment for Ewing's sarcoma involve therapeutic agents that target the expression of the NKX2.2 gene or block the activity of the NKX2.2 protein. Also provided are methods of screening therapeutic agents that affect the expression of the NKX2.2 gene.

8 Claims, 13 Drawing Sheets

OTHER PUBLICATIONS

Hahm, K. B., Cho, K., Lee, C., Im, Y. H., Chang, J., Choi, S. G., Sorensen, P. H., Thiele, C. J., and Kim, S. J. (1999). Repression of the gene encoding the TGF-beta type II receptor is a major target of the EWS-FLI1 oncoprotein. Nat Genet 23, 222-227.

Hu-Lieskovan, S., Heidel, J. D., Bartlett, D. W., Davis, M. E., and Triche, T. J. (2005a). Sequence-specific knockdown of EWS-FLI1 by targeted, nonviral delivery of small interfering RNA inhibits tumor growth in a murine model of metastatic Ewing's sarcoma. Cancer Res 65, 8984-8992.

Hu-Lieskovan, S., Zhang, J., Wu, L., Shimada, H., Schofield, D. E., and Triche, T. J. (2005b). EWS-FLI1 fusion protein up-regulates critical genes in neural crest development and is responsible for the observed phenotype of Ewing's family of tumors. Cancer Res 65, 4633-4644.

Jaishankar, S., Zhang, J., Roussel, M. F., and Baker, S. J. (1999). Transforming activity of EWS/FLI is not strictly dependent upon DNA-binding activity. Oncogene 18, 5592-5597.

Lessnick, S. L., Braun, B. S., Denny, C. T., and May, W. A. (1995). Multiple domains mediate transformation by the Ewing's sarcoma EWS/FLI-1 fusion gene. Oncogene 10, 423-431.

Lessnick, S. L., Dacwag, C. S., and Golub, T. R. (2002). The Ewing's sarcoma oncoprotein EWS/FLI induces a p53-dependent growth arrest in primary human fibroblasts. Cancer Cell 1, 393-401.

May, W. A., Arvand, A., Thompson, A. D., Braun, B. S., Wright, M., and Denny, C. T. (1997). EWS/FLI1-induced manic fringe renders NIH 3T3 cells tumorigenic. Nat Genet 17, 495-497.

May, W. A., Gishizky, M. L., Lessnick, S. L., Lunsford, L. B., Lewis, B. C., Delattre, O., Zucman, J., Thomas, G., and Denny, C. T. (1993a). Ewing sarcoma 11;22 translocation produces a chimeric transcription factor that requires the DNA-binding domain encoded by FLI1 for transformation. Proc Natl Acad Sci U S A 90, 5752-5756.

May, W. A., Lessnick, S. L., Braun, B. S., Klemsz, M., Lewis, B. C., Lunsford, L. B., Hromas, R., and Denny, C. T. (1993b). The Ewing's sarcoma EWS/FLI-1 fusion gene encodes a more potent transcriptional activator and is a more powerful transforming gene than FLI-1. Mol Cell Biol 13, 7393-7398.

McMahon, A. P. (2000). Neural patterning: the role of Nkx genes in the ventral spinal cord. Genes Dev 14, 2261-2264.

Navas-Palacios, J. J., Aparicio-Duque, R., and Valdes, M. D. (1984). On the histogenesis of Ewing's sarcoma. An ultrastructural, immunohistochemical, and cytochemical study. Cancer 53, 1882-1901.

Price, M., Lazzaro, D., Pohl, T., Mattei, M. G., Ruther, U., Olivo, J. C., Duboule, D., and Di Lauro, R. (1992). Regional expression of the homeobox gene Nkx-2.2 in the developing mammalian forebrain. Neuron 8, 241-255.

Prieur, A., Tirode, F., Cohen, P., and Delattre, O. (2004). EWS/FLI-1 silencing and gene profiling of Ewing cells reveal downstream oncogenic pathways and a crucial role for repression of insulin-like growth factor binding protein 3. Mol Cell Biol 24, 7275-7283.

Qi, Y., Cai, J., Wu, Y., Wu, R., Lee, J., Fu, H., Rao, M., Sussel, L., Rubenstein, J., and Qiu, M. (2001). Control of oligodendrocyte differentiation by the Nkx2.2 homeodomain transcription factor. Development 128, 2723-2733.

Smith, R, Owen La, Trem DJ, Wong JS, Whangbo JS, Golub TR, Lessnick SL. (May 2006). Expression profiling of EWS/FLI identifies NKX2.2 as a critical target gene in Ewing's sarcoma. Cancer Cell 9, 405-416.

Staege, M. S., Hutter, C., Neumann, I., Foja, S., Hattenhorst, U. E., Hansen, G., Afar, D., and Burdach, S. E. (2004). DNA microarrays reveal relationship of Ewing family tumors to both endothelial and fetal neural crest-derived cells and define novel targets. Cancer Res 64, 8213-8221.

Teitell, M. A., Thompson, A. D., Sorensen, P. H., Shimada, H., Triche, T. J., and Denny, C. T. (1999). EWS/ETS fusion genes induce epithelial and neuroectodermal differentiation in NIH 3T3 fibroblasts. Lab Invest 79, 1535-1543.

Thompson, A. D., Braun, B. S., Arvand, A., Stewart, S. D., May, W. A., Chen, E., Korenberg, J., and Denny, C. (1996). EAT-2 is a novel SH2 domain containing protein that is up regulated by Ewing's sarcoma EWS/FLI1 fusion gene. Oncogene 13, 2649-2658.

Thompson, A. D., Teitell, M. A., Arvand, A., and Denny, C. T. (1999). Divergent Ewing's sarcoma EWS/ETS fusions confer a common tumorigenic phenotype on NIH3T3 cells. Oncogene 18, 5506-5513.

Welford, S. M., Hebert, S. P., Deneen, B., Arvand, A., and Denny, C. T. (2001). DNA binding domain independent pathways are involved in EWS/FLI1 mediated oncogenesis. J Biol Chem 276, 41977-41984.

Zwerner, J. P., and May, W. A. (2001). PDGF-C is an EWS/FLI induced transforming growth factor in Ewing family tumors. Oncogene 20, 626-633.

* cited by examiner

A

A673 Ewing's sarcoma cells

EtOH 1.5 uM TSA

METHODS AND COMPOSITIONS FOR THE DIAGNOSIS AND TREATMENT OF EWING'S SARCOMA

GOVERNMENT RIGHTS

This invention was made with United States Government support awarded under NIH/NCI K08 CA96755. The United States Government has certain rights in this invention.

FIELD OF THE INVENTION

The invention relates generally to the diagnosis and treatment of a cancer such as Ewing's sarcoma. In particular, it is related to the use of NKX2.2 expression or expression of downstream genes of NKX2.2 as diagnostic markers for Ewing's sarcoma. It is also related to treatments of Ewing's sarcoma which target the expression of NKX2.2.

BACKGROUND OF THE INVENTION

Ewing's sarcoma is an aggressive and highly metastatic malignancy first described by James Ewing in 1921. It arises in and around the bones of the extremities and central skeleton, but may also arise in the soft tissues as "extraosseous Ewing's." Ewing's sarcoma primarily affects children and young adults, predominantly those of European descent, with the highest rates of development occurring in white male adolescents.

Cells of Ewing's sarcoma appear as small, round, undifferentiated blue cells, and thus belongs to a class of tumors with a similar histologic appearance which includes rhabdomyosarcoma, neuroblastoma, and lymphoma. However, the cell of origin of Ewing's sarcoma is unknown. Most cases of Ewing's sarcoma have a recurrent chromosomal translocation, t(11;22)(q24;q12), that encodes a fusion protein, EWS/FLI (Dellatre et al., 1992). The FLI portion contains an ETS family DNA-binding domain while the EWS portion functions as a strong transcriptional activation domain (Dellatre et al., 1992; Lessnick et al., 1995; May et al., 1993a; May et al., 1993b). EWS/FLI is thus an aberrant transcription factor that dysregulates target genes involved in tumor development.

The diagnosis of Ewing's sarcoma is typically based on histologic criteria and associated expression of EWS/FLI. The majority of the translocations code for EWS/FLI. However, a minority of translocations encode fusions that are similar, but not identical to EWS/FLI. Consequently, molecular diagnostics that test for EWS/FLI, such as quantitative PCR, miss approximately 15% of Ewing's sarcoma cases. Immunohistochemistry is a more wide-spread and readily applied technique for diagnosis. The most specific and sensitive immunohistochemical marker for Ewing's sarcoma is CD99 expression. However, CD99 expression is an imperfect marker, as some similar tumors can express CD99.

Treatment of Ewing's sarcoma involves therapies targeting the primary tumor with surgery, radiation, or both. However, in the absence of additional therapy, most patients will relapse with distant metasteses. Current treatment includes systemic chemotherapy to eradicate micrometastatic deposits. These regimens include doxorubicin, vincristine, and cyclophosphamide, alternating with etoposide and ifosfamide. However, these drugs act with little specificity for Ewing's sarcoma and have significant side effects.

Overall, the treatment of Ewing's sarcoma remains problematic. Patients with metastatic disease at presentation have long-term cure rate of less than 30%. In the absence of metastatic disease, the cure rate for Ewing's sarcoma is only 50% to 70%. Quick and early identification can lead to intervention with appropriate treatments with potentially better outcomes.

SUMMARY OF THE INVENTION

In one aspect the present invention identifies and characterizes genes that are differentially expressed in Ewing's sarcoma, along with providing methods for detecting the expression of such genes. These genes and the corresponding encoded proteins have utility, for example, as markers of Ewing's sarcoma and as targets for therapeutic intervention in treating the disease.

The identified markers of Ewing's sarcoma can in turn be used to design specific oligonucleotide probes and primers. When used in combination with nucleic acid amplification procedures, these probes and primers permit the rapid analysis of biopsy core specimens. This analysis will assist physicians in diagnosing Ewing's sarcoma and determining optimal treatment courses for individuals having tumors with varying malignancy. The identified markers of Ewing's sarcoma can also be used to generate antibodies capable of specifically binding to the polypeptides encoded by these markers. These antibodies can also be used in diagnostic procedures to permit the identification and diagnosis of Ewing's sarcoma cells, using techniques well-known in the art, e.g. immunohistochemical staining.

In some aspects, the present invention also provides compositions and methods for the treatment of Ewing's sarcoma. In some aspects, the invention comprises methods of treating individuals with Ewing's sarcoma by providing effective amounts of antibodies, DNA molecules, or other therapeutic agents, which interfere with the expression or activity of the above-mentioned genes or gene products.

In one embodiment, the present invention provides methods of diagnosing Ewing's sarcoma comprising detecting in a test sample of cells to be analyzed for Ewing's sarcoma the expression of NKX2.2 or one or more NKX2.2 downstream genes, wherein the downstream genes are up- or down-regulated by NKX2.2 in cells of Ewing's sarcoma; and comparing the expression of NKX2.2 or one or more of the downstream genes in the test sample to the expression of NKX2.2 or one or more of the downstream genes in a control, wherein the control comprises cells where Ewing's sarcoma is absent, and wherein a difference in expression between the test sample and the control indicates cells of Ewing's sarcoma in the sample.

In some methods for diagnosing Ewing's sarcoma, the expression of NKX2.2 or one or more of the downstream genes is detected by measuring the amount of mRNA transcript of NKX2.2 or one or more of the downstream genes present in the sample. Measuring the amount of mRNA transcript of NKX2.2 or one or more of the downstream genes present in the sample may comprise amplifying the transcript of NKX2.2 or one or more of the downstream genes by PCR and detecting the amplification products. Alternatively, measuring the amount of mRNA transcript of NKX2.2 or one or more of the downstream genes present in the sample may comprise microarray analysis.

In some methods for diagnosing Ewing's sarcoma, the expression of NKX2.2 or one or more of the NKX2.2 downstream genes is detected by measuring the amount of protein of NKX2.2 or one or more of the downstream genes present in the sample. Measuring the amount of protein from NKX2.2 or one or more of the downstream genes may comprise contacting the sample with an antibody or antibody fragment, under conditions suitable for specific binding of the antibody or antibody fragment to the protein. The antibody may be a polyclonal or monoclonal antibody.

In one embodiment, the present invention provides methods of diagnosing Ewing's sarcoma comprising detecting in a test sample of cells to be analyzed for Ewing's sarcoma the expression of NKX2.2; and comparing the expression of NKX2.2 in the test sample to the expression of NKX2.2 in a control, wherein the control comprises cells where Ewing's sarcoma is absent, and wherein a difference in expression between the test sample and the control indicates cells of Ewing's sarcoma in the sample.

In some methods for diagnosing Ewing's sarcoma, the expression of NKX2.2 is detected by measuring the amount of mRNA transcript of NKX2.2 present in the sample. Measuring the amount of mRNA transcript of NKX2.2 may comprise amplifying the NKX2.2 transcript by PCR with at least one NKX2.2 specific primer to provide NKX2.2 amplification products and observing the NKX2.2 amplification products. Alternatively, measuring the amount of mRNA transcript of NKX2.2 present in the sample may comprise microarray analysis.

In some methods, the expression of NKX2.2 or one or more of the NKX2.2 downstream genes is detected by measuring the amount of protein present in the sample. Measuring the amount of NKX2.2 protein present in the sample may comprise contacting the sample with an anti-NKX2.2 antibody or antibody fragment, under conditions suitable for specific binding of the anti-NKX2.2 antibody or antibody fragment to the NKX2.2 protein. The anti-NKX2.2 antibody may be a polyclonal antibody, a monoclonal antibody. The anti-NKX2.2 antibody fragment may be a Fab fragment or a single chain antibody.

In some methods the expression of NKX2.2 is detected by measuring the activity of the NKX2.2 protein present in the sample. For example, the activity of the NKX2.2 protein to be measured may be DNA binding activity.

In one embodiment, the present invention provides a composition comprising a therapeutic agent and a pharmaceutically acceptable carrier, wherein the therapeutic agent is an agent capable of mediating NKX2.2-specific RNA interference or a histone deacetylase inhibitor, and wherein the therapeutic agent is present in an effective amount to reduce the expression or block activity of NKX2.2 in cancerous cells exposed to the therapeutic agent.

In some compositions, the therapeutic agent may be an agent capable of mediating NKX2.2-specific RNA interference or a histone deacetylase inhibitor. Agents capable of mediating NKX2.2-specific RNA interference may comprise a vector encoding one or more siRNAs. The siRNAs may target a sequence corresponding to NKX2.2. The vector may be introduced into a cell using a retrovirus. Agents capable of mediating NKX2.2-specific RNA interference may also be an oligonucleotide. The oligonucleotide may have RNA interference activity and may be an siRNA corresponding to NKX2.2. In some compositions, the siRNA targets the sequence having at least 95% sequence identity to SEQ ID NO: 12. Where the therapeutic agent is a histone deacetylase inhibitor, the histone deacetylase inhibitor may be selected from suberoylanilide hydroxamic acid or Trichostatin A (TSA).

In one aspect, the present invention includes methods of administering to a subject having or suspected of having Ewing's sarcoma a pharmaceutical composition comprising a therapeutic agent and a pharmaceutically acceptable carrier, wherein the therapeutic agent is an oligonucleotide or a histone deacetylase inhibitor, and wherein the therapeutic agent is present in an effective amount to reduce the expression or activity of NKX2.2 in cancerous cells exposed to the therapeutic agent, and wherein the pharmaceutical composition treats Ewing's sarcoma.

In one embodiment, the present invention provides methods of screening for therapeutic agents for Ewing's sarcoma, the method comprising applying an amount of a therapeutic agent that may be effective in treating Ewing's sarcoma to a test organism, cell, or lysate; and measuring the effect of the agent on either the expression of NKX2.2 or one or more NKX2.2 downstream genes, or the activity of NKX2.2 or one or more NKX2.2 downstream proteins. Such methods may further include selecting those agents that diminish NKX2.2 gene expression or NKX2.2 protein activity, or alter the expression of downstream genes.

BRIEF DESCRIPTION OF THE DRAWINGS

FIG. 1C shows the 33 genes that were upregulated by EWS/FLI in all four replicates from FIG. 1A as the geneset. The rank ordered list was the list from FIG. 1B. FIG. 1D shows some of the 180 genes that were downregulated by EWS/FLI in all four replicates from FIG. 1A as the geneset.

FIG. 3A shows RT-PCR analysis demonstrating that NKX2.2 transcript is expressed in four different patient-derived Ewing's sarcoma tumor samples. FIG. 3B is a graphical representation of NKX2.2 expression levels across 181 sarcoma tumor samples.

DETAILED DESCRIPTION

Figure 1:
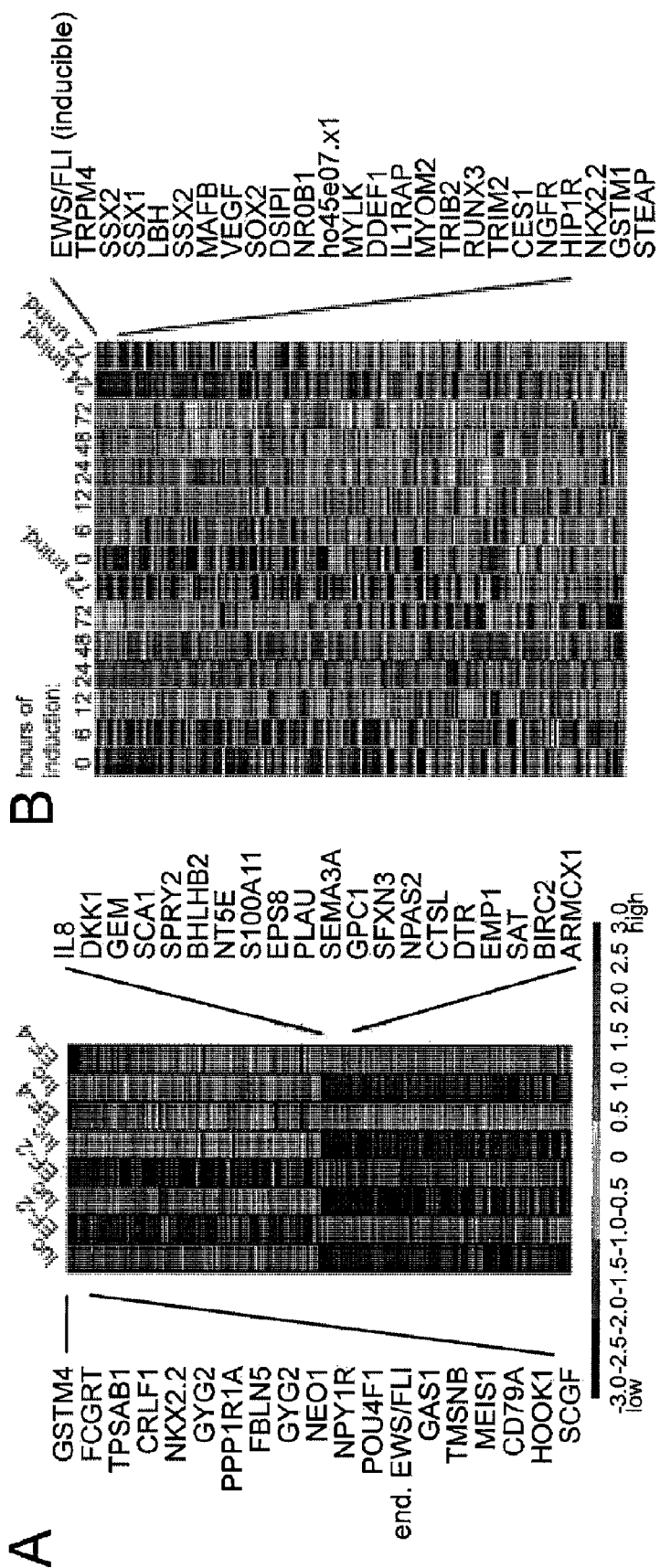
FIG. 1 shows microarray analysis of A673 cells with EWS/FLI RNAi.
Figure 1:
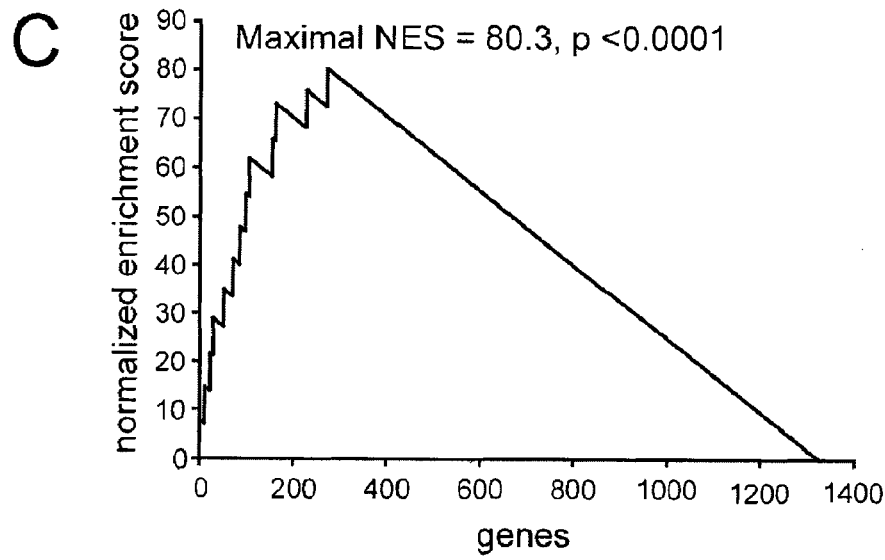
Figure 1:
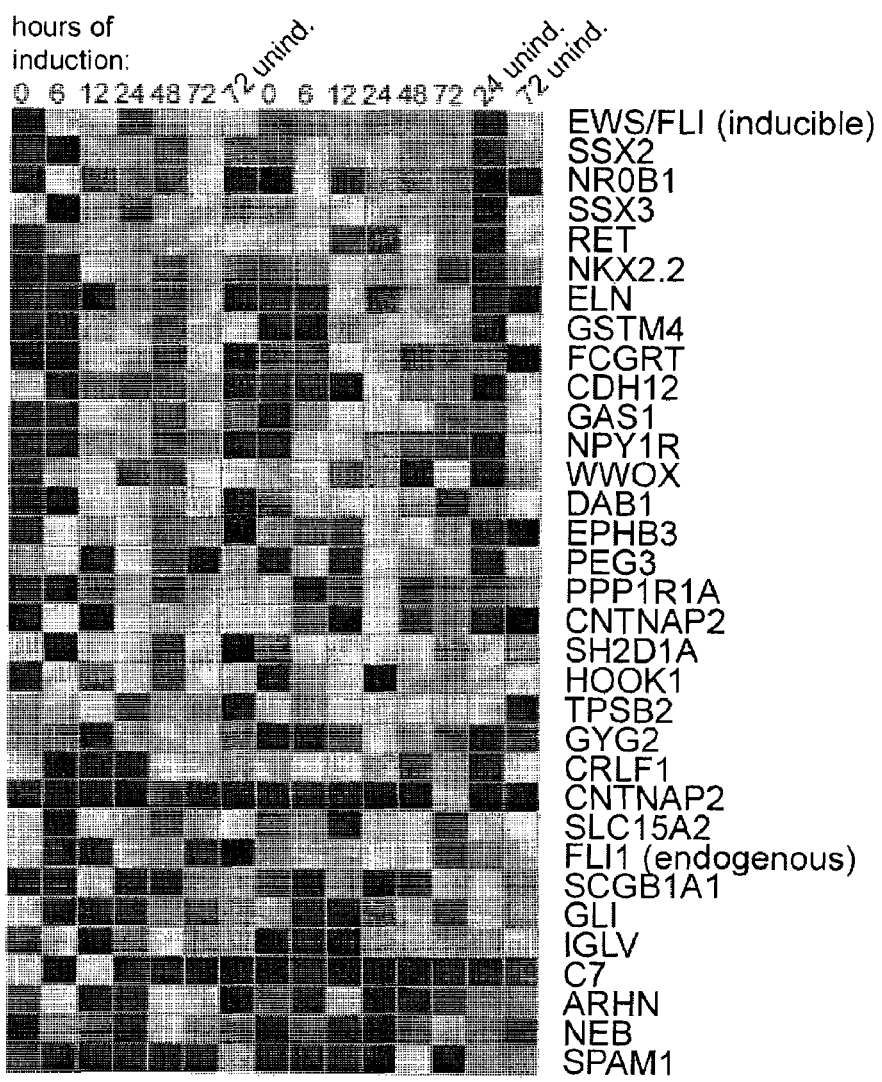
Figure 1:
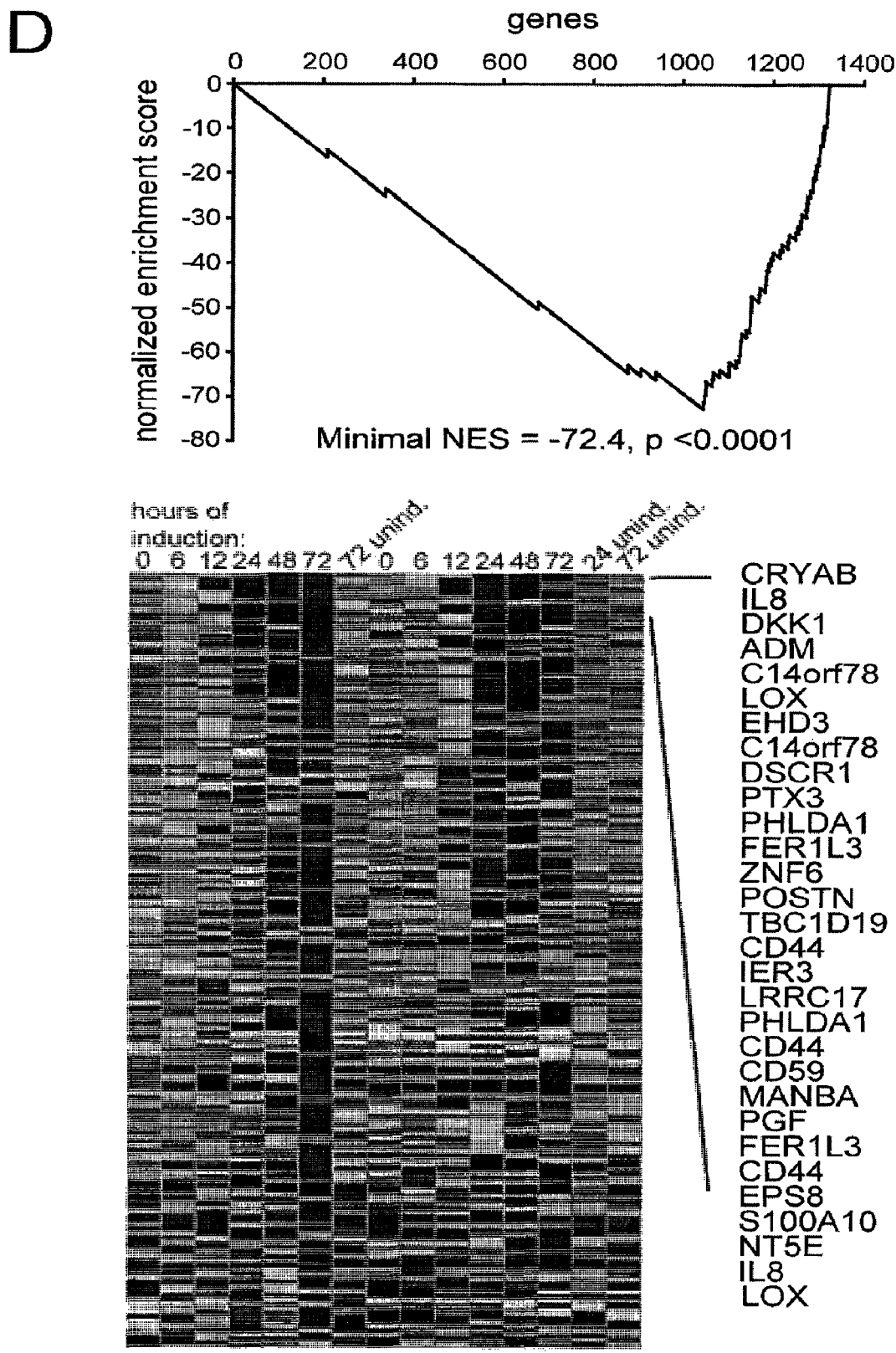

Disclosed herein are methods and compositions for the detection and treatment of Ewing's sarcoma. In particular, the methods of detection relate to measuring the expression of the NKX2.2 gene or one or more NKX2.2 downstream genes in samples of Ewing's sarcoma cells. The compositions and methods of treatment for Ewing's sarcoma involve therapeutic agents that target the expression of the NKX2.2 gene or inhibit the activity of the NKX2.2 protein. Also provided are methods of screening therapeutic agents that affect the expression of the NKX2.2 gene.

The identification of EWS/FLI over a decade ago suggested that more specific and less toxic therapies for Ewing's sarcoma would be feasible (Dellatre et al., 1992). Unfortunately, this hope has not been realized. Now, the present inventor has discovered that the NKX2.2 gene is specifically upregulated in Ewing's sarcoma cells. The NKX2.2 gene had not been previously implicated in cancer development, but functional studies revealed that NKX2.2 is absolutely required for oncogenic transformation in Ewing's sarcoma cells. Thus, NKX2.2 provides a good diagnostic marker for Ewing's sarcoma and a target for the treatment of the disease in a way that was not possible using EWS/FLI.

While not wishing to be limited by theory, it is believed that NKX2.2 is upregulated by the aberrant transcription factor EWS/FLI, a product of the chromosomal translocations in many Ewing's sarcomas. NKX2.2 is a member of the NK2 family of homeobox genes (Kim and Nirenberg, 1989). NKX2.2 is expressed in the developing forebrain and spinal cord, and is thought to underlie neuronal development, patterning, and fate specification of neurons and oligodendrocytes (McMahon, 2000; Price et al., 1992; Qi et al., 2001). NKX2.2 had not been previously implicated in cancer development. While the cell of origin of Ewing's sarcoma is unknown, one prevailing theory is that it is derived from the neural crest (e.g., Cavenzzana et al., 1987; Collini et al., 2003; Staege et al., 2004). Importantly, however, the neural crest phenotype may be a consequence of EWS/FLI expression, rather than being related to the cell of origin of the tumor (Hu-Lieskovan et al., 2005b; Teitell et al., 1999; Thompson et al., 1999). As an EWS/FLI target gene, NKX2.2 may thus contribute to the neural characteristics of the tumor.

Because NKX2.2 is a critical EWS/FLI target gene, it has superior diagnostic and therapeutic features, not identified in other EWS/FLI targets. First, it was discovered that NKX2.2 is not only expressed in Ewing's sarcoma cell lines, but is also expressed in primary patient-derived tumor samples. Furthermore, because NKX2.2 is expressed in Ewing's sarcoma cells, but not in normal cells or in other types of cancer cells, it makes an ideal marker. Because most tumor samples contain mixed populations of both normal and transformed cells, a marker expressed in normal cells will cause a "background" signal that may mask the presence of transformed cells. Therefore, a marker specific to Ewing's sarcoma cells, such as NKX2.2, is particularly desirable.

A new, sensitive marker is important because the diagnosis of Ewing's sarcoma has traditionally been based on the histologic appearance of the tumor and an appropriate immunohistochemical staining pattern. The main immunohistochemical marker for Ewing's sarcoma is CD99 (also called MIC2; Ambros et al., 1991). CD99 expression is not specific to Ewing's sarcoma, and can also be found on lymphocytes and other hematopoietic cells, endothelial cells, and other tumor types (Choi et al., 2001; Dworzak et al., 1994; Matias-Guiu et al., 1998; Schenkel et al., 2002). While EWS/FLI and other translocations are thought to be highly specific for Ewing's sarcoma, molecular tests for these translocations are not universally applied to biopsy specimens due to problems with PCR amplification of EWS/FLI. This new marker increases the diagnostic specificity for this tumor.

Second, NKX2.2 may also serve as a therapeutic target for Ewing's sarcoma. The present inventor has shown that loss of NKX2.2 expression via RNAi or inhibition of NKX2.2 function with a histone deacetylase inhibitor results in a loss of oncogenic transformation or inhibition of cell growth. Therefore, therapeutic approaches directed against NKX2.2 have clinical value for patients with this disease.

In addition to NKX2.2, the present invention provides that genes which are up-regulated or down-regulated by the NKX2.2 gene (i.e. "downstream genes") may be used as diagnostic markers. As a transcription factor, NKX2.2 regulates the expression of a number of target genes that are involved in the oncogenesis of Ewing's sarcoma. Thus, as the expression of NKX2.2 is upregulated in Ewing's sarcoma cells, the expression of the downstream genes will be increased or decreased, depending on the effect that NKX2.2 has on that particular gene. Consequently, one or more these downstream genes could be used as markers for Ewing's sarcoma.

Definitions

The present invention is described herein using several definitions, as set forth below and throughout the specification.

As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

As used herein, the term "administer" includes any route of introducing or delivering to a subject a compound to perform its intended function. Administration can be carried out by any suitable route, including orally, intranasally, parenterally (intravenously, intramuscularly, intraperitoneally, or subcutaneously), or topically.

As used herein, "amplification" or "amplifying" refers to the production of additional copies of a nucleic acid sequence. Amplification is generally carried out using polymerase chain reaction (PCR) technologies known in the art. The "amplification mixture" refers to an aqueous solution comprising the various reagents used to amplify a target nucleic acid. These may include enzymes (e.g., a thermostable polymerase), aqueous buffers, salts, amplification primers, target nucleic acid, and nucleoside triphosphates, and optionally at least one labeled probe and/or optionally at least one agent for determining the melting temperature of an amplified target nucleic acid (e.g., a fluorescent intercalating agent that exhibits a change in fluorescence in the presence of double-stranded nucleic acid). Optionally, the amplification mixture may include a reverse transcriptase enzyme used to make a cDNA copy of RNA. Amplification of nucleic acids may include amplification of nucleic acids or subregions or fragments of these nucleic acids. For example, amplification may include amplifying portions of nucleic acids between 20 and 300 bases long by selecting the proper primer sequences and using PCR.

As used herein the term "antibody" refers to an immunoglobulin and any antigen-binding portion of an immunoglobulin (e.g. IgG, IgD, IgA, IgM and IgE) i.e., a polypeptide that contains an antigen binding site, which specifically binds ("immunoreacts with") an antigen. Antibodies can comprise at least one heavy (H) chain and at least one light (L) chain inter-connected by at least one disulfide bond. The term "$V_H$" refers to a heavy chain variable region of an antibody. The term "$V_L$" refers to a light chain variable region of an antibody. In exemplary embodiments, the term "antibody" specifically covers monoclonal and polyclonal antibodies. A "polyclonal antibody" refers to an antibody which has been derived from the sera of animals immunized with an antigen or antigens. A "monoclonal antibody" refers to an antibody produced by a single clone of hybridoma cells.

As used herein, "biological activity" refers to the activity of the protein in vivo or to its activity in conventional in vitro and in vivo biological assays designed to test its functionality. Biological activity may refer to a protein's enzymatic activity or the protein's ability to bind other proteins or ligands, or both.

As used herein, the term "detection" or "detecting" includes any suitable method of assaying or measuring the expression level of a gene or a gene product in a cell or a sample of cells. In some embodiments, the expression level of a gene may be assayed by measuring the amount of mRNA transcribed from the genomic DNA. In some embodiments, the expression level of a gene may be assayed by measuring the amount of protein translated from the mRNA. In some embodiments, the expression level of a gene may be assayed by measuring the biochemical activity exhibited by the translated polypeptide. The expression level is measured relative to a control sample.

As used herein, the term "downstream gene" refers to any gene whose expression (up or down) is regulated by another gene or gene product, i.e. an "upstream gene". In the context of the present invention, NKX2.2 is an example of an upstream gene, which regulates (up or down) the expression of one or more NKX2.2 downstream genes.

A "fragment" in the context of a nucleic acid refers to a sequence of nucleotide residues which are at least about 5 nucleotides, at least about 7 nucleotides, at least about 9 nucleotides, at least about 11 nucleotides, or at least about 17 nucleotides. The fragment is typically less than about 300 nucleotides, less than about 100 nucleotides, less than about 75 nucleotides, less than about 50 nucleotides, or less than 30 nucleotides. In certain embodiments, the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention. In some embodiments, the fragment comprises a sequence substantially similar to a portion of NKX2.2.

A "fragment" in the context of a polypeptide is a stretch of amino acid residues of at least about 5 amino acids, at least about 7 amino acids, at least about 9 amino acids, or at least about 13 or more amino acids. The peptide typically is less than about 50 amino acids, or less than 30 amino acids. In many embodiments, the peptide is from about five to about 35 amino acids. To be active, any polypeptide must have sufficient length to display biological and/or immunological activity. The term "immunogenic" refers to the capability of the natural, recombinant or synthetic NKX2.2-like peptide, or any peptide thereof, to induce a specific immune response in appropriate animals or cells and to bind with specific antibodies.

As used herein, the terms "gene expression" or "expression" refer to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "introduce" refers to the incorporation of a nucleic acid into a eukaryotic or prokaryotic cell where the nucleic acid may be incorporated into the genome of the cell (e.g., chromosome, plasmid, plastid, or mitochondrial DNA), converted into an autonomous replicon, or transiently expressed (e.g., transfected mRNA). The term includes such nucleic acid introduction means as transfection, transformation, and transduction.

As used herein, "microarray" or "array" refers to an arrangement of a collection of nucleic acids (e.g., nucleotide sequences) in a centralized location. Arrays can be on a solid substrate, such as a glass slide, or on a semi-solid substrate, such as nitrocellulose membrane. The nucleotide sequences can be DNA, RNA, or any combination or permutations thereof. The nucleotide sequences can also be partial sequences or fragments from a gene, primers, whole gene sequences, non-coding sequences, coding sequences, published sequences, known sequences, or novel sequences.

As used herein, "nucleic acid," "nucleotide sequence," or "nucleic acid sequence" refer to a nucleotide, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. RNA may be used in the methods described herein and/or may be converted to cDNA by reverse-transcription for use in the methods described herein.

An "oligonucleotide" is a nucleic acid that includes at least two nucleotides. Oligonucleotides used in the methods disclosed herein typically include at least about 10 nucleotides and more typically at least about 15 nucleotides. An oligonucleotide may be designed to function as a "primer" for PCR or reverse transcription. A "primer" is a short nucleic acid, usually a single strand DNA oligonucleotide, which may be annealed to a target polynucleotide by complementary base-pairing. The primer may then be extended along the target DNA strand by a DNA polymerase enzyme. If the target is RNA, a primer may anneal and then be extended by a reverse transcriptase enzyme. Primer pairs can be used for amplification (and identification) of a nucleic acid sequence (e.g., by the polymerase chain reaction (PCR)). An oligonucleotide may also be designed to function as a "probe" for microarray analysis or PCR analysis (e.g. TaqMan® assays).

Oligonucleotides as described herein typically are capable of forming hydrogen bonds with oligonucleotides having a complementary base sequence. As described herein, a first sequence of an oligonucleotide is described as being 100% complementary with a second sequence of an oligonucleotide when the consecutive bases of the first sequence (read 5' to 3') follow the Watson-Crick rule of base pairing as compared to the consecutive bases of the second sequence (read 3' to 5').

An oligonucleotide may include nucleotide substitutions. An oligonucleotide that is specific for a target nucleic acid also may be specific for a nucleic acid sequence that has "homology" to the target nucleic acid sequence. As used herein, "homology" refers to sequence similarity or, interchangeably, sequence identity, between two or more polynucleotide sequences or two or more polypeptide sequences. The terms "percent identity" and "% identity" as applied to polynucleotide sequences, refer to the percentage of residue matches between at least two polynucleotide sequences aligned using a standardized algorithm (e.g., BLAST). An oligonucleotide that is specific for a target nucleic acid will "hybridize" to the target nucleic acid under suitable conditions. As used herein, "hybridization" or "hybridizing" refers to the process by which a oligonucleotide single strand anneals with a complementary strand through base pairing under defined hybridization conditions. "Specific hybridization" is an indication that two nucleic acid sequences share a high degree of complementarity. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J. Oligonucleotides used as specific primers for amplifying a target nucleic acid generally are capable of specifically hybridizing to the target nucleic acid.

As used herein, the terms "polypeptide," "peptide," and "protein" are used interchangeably to refer to a polymer of amino acid residues. The terms apply to amino acid polymers in which one or more amino acid residues is an artificial chemical analog of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms polypeptide, peptide, and protein are also inclusive of modifications including, but not limited to, glycosylation, lipid attachment, sulfation, carboxylation, hydroxylation, ADP-ribosylation, and addition of other complex polysaccharides.

As used herein, the term "RNA interference" (RNAi) refers to the process of sequence-specific post-transcriptional gene silencing mediated by short interfering nucleic acids (siRNAs). The term "agent capable of mediating RNA interference" refers to siRNAs as well as DNA and RNA vectors that encode siRNAs when transcribed within a cell.

As used herein, the term "siRNA" refers to short interfering nucleic acid. The term is meant to be equivalent to other terms used to describe nucleic acid molecules that are capable of mediating sequence specific RNA interference, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others.

As used herein, the term "therapeutically effective amount" refers to the quantity of a compound that alleviates, in whole or in part, symptoms associated with a disorder or disease, or halts of further progression or worsening of those symptoms, or prevents or provides prophylaxis for the disease or disorder in a subject at risk for developing the disease or disorder.

As used herein, the term "sample" is used in its broadest sense. A sample may include a bodily tissue (e.g. a biopsy core specimen) or a bodily fluid including but not limited to blood (or a fraction of blood such as plasma or serum), lymph, mucus, tears, urine, and saliva. A sample may include an extract from a cell, a chromosome, organelle, or a virus. A sample may be a "cell-free" sample, meaning that the volume of cells in the sample are less than about 2% of the total sample volume. A sample may comprise DNA (e.g., genomic DNA), RNA (e.g., mRNA), and cDNA, any of which may be amplified to provide amplified nucleic acid. For example, a sample may include nucleic acid in solution or bound to a substrate (e.g., as part of a microarray). A sample may be obtained from any patient. In particular, a sample may be obtained from a patient having or suspected to be at risk for Ewing's sarcoma and may be a biopsy sample.

As used herein, "treatment" or "treating" within the context of the instant invention, mean an alleviation of symptoms associated with a disorder or disease, or inhibition, halt, or reversal of further progression or worsening of those symptoms, or prevention or prophylaxis of the disease or disorder. For example, within the context of the instant invention, successful treatment may include an alleviation of symptoms related to a cancerous growth by the Ewing's sarcoma, or an inhibiting or halting in the progression of the Ewing's sarcoma or in the growth or metastasis of Ewing's sarcoma cells, or a regression or partial or complete remission of the Ewing's sarcoma, disease stabilization, or an increase in the overall survival of the Ewing's sarcoma patient.

Methods of Detection

In some aspects, the present invention relates to diagnostic methods useful in assessing patients who are suspected of having Ewing's sarcoma. The methods are based, in part, on the analysis of gene expression in Ewing's sarcoma cells. The present inventor found that levels of gene expression for NKX2.2 and one or more of its downstream target genes could identify Ewing's sarcoma cells with great specificity and sensitivity.

In some methods, the level of gene expression can be determined by assessing the amount of one or more mRNAs in the test sample. Methods of measuring mRNA in samples are known in the art. To measure mRNA levels, the cells in the samples can be lysed and the levels of mRNA in the lysates or in RNA purified or semi-purified from lysates can be measured by any variety of methods familiar to those in the art. Such methods include, without limitation, hybridization assays using detectably labeled DNA or RNA probes (i.e. Northern blotting) or quantitative or semi-quantitative RT-PCR methodologies using appropriate oligonucleotide primers. Alternatively, quantitative or semi-quantitative in situ hybridization assays can be carried out using, for example, tissue sections, or unlysed cell suspensions, and detectably labeled (e.g. fluoresecent, or enzyme-labeled) DNA or RNA probes. Additional methods for quantifying mRNA include RNA protection assay (RPA), cDNA and oligonucleotide microarrays, representation difference analysis (RDA), differential display, EST sequence analysis, serial analysis of gene expression (SAGE), and LMF (multiplex ligation-mediated amplification with the Luminex FlexMAP, See Peck et al., Genome Biol. 2006; 7(7):R61).

In suitable embodiments, PCR amplification is used to detect NKX2.2 or one or more NKX2.2 downstream genes in the test sample. Briefly, in PCR, two primer sequences are prepared that are complementary to regions on opposite complementary strands of the marker sequence, e.g. NKX2.2 or one or more NKX2.2 downstream genes. An excess of deoxynucleotide triphosphates are added to a reaction mixture along with a DNA polymerase, e.g., Taq polymerase. If the target sequence is present in a sample, the primers will bind to the sequence and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated, thereby generating amplification products. A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990.

Any suitable fragment of NKX2.2 or one or more of the downstream genes may be amplified and detected. Designing efficient primers for PCR is within the ordinary skill in the art. Typically, amplified fragments for detection will be approximately 50 to 300 nucleotides in length. One or more of the downstream genes can be selected from the list of downstream targets identified in Table 5 below.

Amplification products may be detected in several ways. Amplification products may be visualized by electrophoresis of the sample in a gel and then staining with a DNA binding dye, e.g. ethidium bromide. Alternatively, the amplification products may be integrally labeled with a radio- or fluorescence nucleotide and then visualized using x-ray film or under the appropriate stimulating spectra.

Amplification may be also monitored using "real-time" methods. Real time PCR allows for the detection and quantitation of a nucleic acid target. Typically, this approach to quantitative PCR utilizes a fluorescent dye, which may be a double-strand specific dye, such as SYBR Green® I. Alternatively, other fluorescent dyes (e.g. FAM or HEX) may be conjugated to an oligonucleotide probe or a primer. Various instruments capable of performing real time PCR are known in the art and include, for example, ABI Prism® 7900 (Applied Biosystems) and LightCycler® systems (Roche). The fluorescent signal generated at each cycle of PCR is proportional to the amount of PCR product. A plot of fluorescence versus cycle number is used to describe the kinetics of amplification and a fluorescence threshold level is used to define a fractional cycle number related to initial template concentration. When amplification is performed and detected on an instrument capable of reading fluorescence during thermal cycling, the intended PCR product from non-specific PCR products can be differentiated using melting analysis. By measuring the change in fluorescence while gradually increasing the temperature of the reaction subsequent to amplification and signal generation it may be possible to determine the $T_m$ of the intended product(s) as well as that of the nonspecific product.

The methods may include amplifying multiple nucleic acids in sample, also known as "multiplex detection" or "multiplexing." As used herein the term "multiplex PCR" refers to PCR, which involves adding more than one set of PCR primers to the reaction in order to detect and quantify multiple nucleic acids, including nucleic acids from one or more target gene markers. Furthermore, multiplexing with an internal control (e.g., 18s rRNA, GADPH, or 0-actin) provides a control for the PCR without reaction.

The methods may include measuring the level of mRNA transcript of NKX2.2 or one or more NKX2.2 downstream genes using a microarray. Microarrays are an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675 1680) and Schena, M. et al. (1996; Proc. Natl. Acad. Sci. 93: 10614 10619), all of which are incorporated herein in their entirety by reference. In other embodiments, such arrays are produced by the methods described by Brown et al., U.S. Pat. No. 5,807,522. The microarray is preferably composed of a large number of unique, single-stranded nucleic acid sequences, usually either synthetic antisense oligonucleotides or fragments of cDNAs, fixed to a solid support. Polynucleotides used in the microarray may be oligonucleotides or fragments that are specific to a gene or genes of interest, e.g. NKX2.2 (SEQ ID NO: 1) or one or more NKX2.2 downstream genes.

In one embodiment of the invention, fluorescence-labeled single strand (or "first strand") cDNA probe is made from total or mRNA by first isolating RNA from the sample of cells to be tested for Ewing's sarcoma and cells of a control. Typically, the two cDNA samples are labeled with different fluorescent dyes (e.g. green Cy3 and red Cy5). The two labeled cDNA samples are mixed and hybridized to the microarray, and the slide is scanned. In the resulting image, the green Cy3 and red Cy5 signals are overlaid—yellow spots indicate equal intensity for the dyes. With the use of image analysis software, signal intensities are determined for each dye at each element of the array, and the logarithm of the ratio of Cy5 intensity to Cy3 intensity is calculated (center). Positive log(Cy5/Cy3) ratios indicate relative excess of the transcript in the Cy5-labeled sample, and negative log(Cy5/Cy3) ratios indicate relative excess of the transcript in the Cy3-labeled sample. Values near zero indicate equal abundance in the two samples.

In suitable embodiments, the level of gene expression can be determined by assessing the amount of one or more proteins of NKX2.2 or one or more NKX2.2 downstream genes in the test sample. Methods of measuring proteins levels in a test sample are also known in the art. Many of these methods employ antibodies (e.g. monoclonal or polyclonal antibodies) that bind specifically to a target protein. In such assays, the antibody itself or a secondary antibody that binds to it can be detectably labeled. Alternatively, the antibody can be conjugated with biotin and detectably labled avidin or streptavidin (polypeptides that bind to biotin) can be used to detect the presence of the biotinylated antibody. Combinations of these approaches (including "multi-layer sandwich" assays), which are also familiar to those of ordinary skill in the art, can be used to enhance the sensitivity of the methodologies. Some of these protein measuring assays (e.g. ELISA or Western blot) can be applied to bodily fluids or lysates of test cells, while others (e.g. immunohistological methods or fluorescence flow cytometry) are better suited for application to histological sections or unlysed cell suspensions. Methods of measuring the amount of label will depend on the nature of the label and are known in the art. Appropriate labels include, without limitation, radionuclides (e.g. $^{125}I$, $^{131}I$, $^{35}S$, $^{3}H$, or $^{32}P$), enzymes (e.g. alkaline phosphatase, horseradish peroxidase, luciferase, or β-galactosidase), fluorescent moieties or proteins (e.g. fluorescein, rhodamine, phycoerythrin, a GFP, or a BFP), or luminescent moieties. Other applicable assays include quantitative immunoprecipitation or complement fixation assays.

Various types of antibodies or antibody fragments and constructs may be used in accordance with the present invention. Such antibodies include monoclonal and polyclonal antibodies, single chain antibodies, chimeric antibodies, bifunctional/bispecific antibodies, humanized antibodies, human antibodies, and complementary determining region (CDR)-grafted antibodies, including compounds that include CDR and/or antigen-binding sequences, which specifically recognize NKX2.2 or one or more of the proteins encoded by NKX2.2 downstream target genes.

Antibody fragments, including Fab, Fab', F(ab')$_2$, and F$_v$, and engineered constructs are also useful. In some aspects, the present invention includes the use of antibody fragments. Antibody fragments can be prepared by proteolytic hydrolysis of an antibody or by expression in *E. coli* of the DNA coding for the fragment. Antibody fragments can be obtained by pepsin or papain digestion of whole antibodies. For example, antibody fragments can be produced by enzymatic cleavage of antibodies with pepsin to provide a fragment denoted F(ab')$_2$. This fragment can be further cleaved using a thiol reducing agent, and optionally a blocking group for the sulfhydryl groups resulting from cleavage of disulfide linkages, to produce Fab' monovalent fragments. Alternatively, an enzymatic cleavage using pepsin produces two monovalent Fab fragments and an Fc fragment directly. These methods have been previously described in U.S. Pat. Nos. 4,036,945 and 4,331,647, Nisonoff et al., Arch Biochem. Biophys. 89:230 (1960); Porter, Biochem. J. 73:119 (1959), and Edelman et al., Meth. Enzymol. 1:422 (1967). Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody. For example, Fv fragments comprise an association of $V_H$ and $V_L$ chains, which can be noncovalent. Alternatively, the variable chains can be linked by an intermolecular disulfide bond or cross-linked by chemicals such as glutaraldehyde.

Typically, the antibody or antibody fragment will bind specifically or specifically recognize a particular target antigen. With respect to antibodies and antibody fragments, the term "specific for" or "specifically recognizes" indicates that the variable regions of the antibodies recognize and bind NKX2.2 or one or more NKX2.2 downstream gene products (i.e., the variable regions are able to distinguish NKX2.2 or one or more NKX2.2 downstream gene products from other similar polypeptides despite sequence identity, homology, or similarity found in the family of polypeptides). An antibody "specifically recognizes" an antigen or an epitope of an antigen if the antibody binds preferably to the antigen over most other antigens. Typically specific binding results in a much stronger association between the antibody binding site and the target antigen than between the antibody binding site and non-target molecule. For specific binding, the affinity constant of the antibody binding site for its cognate antigen may be at least $10^7$, at least $10^8$, at least $10^9$, preferably at least $10^{10}$, or more preferably at least $10^{11}$ liters/mole. Screening assays in which one can determine binding specificity of an antibody are well known and routinely practiced in the art. For an example of how to determine the binding specificity of an antibody, see Chapter 6, Antibodies A Laboratory Manual, Eds. Harlow, et al., Cold Spring Harbor Laboratory; Cold Spring Harbor, N.Y. (1988)).

Methods of making antibodies are known in the art. For polyclonal antibodies, antibody-containing antiserum is isolated from the immunized animal and is screened for the presence of antibodies with the desired specificity using one of the above-described procedures. For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell that produces an antibody with the desired characteristics. These include screening the hybridomas with an ELISA assay, Western blot analysis, or radioimmunoassay (Lutz et al., Exp. Cell Res. 175:109-124 (1988)). Hybridomas secreting the desired antibodies are cloned and the class and subclass are determined using procedures known in the art (Campbell, A. M., Monoclonal Antibody Technology: Laboratory Techniques in Biochemistry and Molecular Biology, Elsevier Science Publishers, Amsterdam, The Netherlands (1984)). Techniques described for the production of single chain antibodies can be adapted to produce single chain antibodies NKX2.2 or one or more of the proteins encoded by NKX2.2 downstream target genes. Generally, techniques for single chain antibodies are demonstrated in U.S. Pat. No. 4,946,778.

In some methods of diagnosing Ewing's sarcoma, the level of gene expression can be determined by assessing the biological activity of one or more proteins in the test sample. For example, the biological activity of NKX2.2 may be assayed. As described above, NKX2.2 is a homeobox protein known to bind specific sequences of DNA. For example, see J Biol. Chem. 2005 Apr. 22; 280(16):16284-94, or J Biol. Chem. 2003 Jan. 10; 278(2):751-6, or Proc Natl Acad Sci USA. 2000 Aug. 15; 97(17):9443-8. These sequences could be used in an electrophoretic mobility shift assay. In this assay, the electrophoretic mobility of a labeled DNA fragment is determined in the presence and absence of the NKX2.2 DNA-binding protein, causing a shift in the location of the fragment band detected by auto radiography or other means. The specificity of the test may be increased via an ELISA type assay by introducing a "supershift" using an NKX2.2 specific antibody to prove that the DNA binding protein identified is indeed NKX2.2.

The level of gene expression in the test sample, as measured by mRNA level, protein level, or activity level, can be compared with the level(s) observed in a control sample. Those of ordinary skill in the art are well able to design appropriate controls. A control may be any sample of cells where Ewing's sarcoma is absent. For example, a control sample may be non-cancerous cells, including, but not limited to normal human fibroblasts, human umbilical endothelial cells (HUVECs), or mesenchymal stem cells, which may be the cell of origin of Ewing's sarcoma. See Cancer Cell 11, 421-29 (2007). A control sample may further include any tumor cell type that is not Ewing's sarcoma including, for example, HEK293, HeLa, HCT116, MCF7, 501MEL, LNCaP, PC3, BT-20, SK-BR-3, and SK-OV-3. Also, any other pediatric tumor type where Ewing's sarcoma is absent would be an appropriate control sample. These could include HOS, OST, SAOS, MG-63, U2OS, RD, TTC442, CCL-136, HR, JR, RH28, RH30, Birch, CHLA 20, CHP 126, and CHLA 90. It may also be useful to compare the level of gene or protein expression to the level of expression of certain constituitively active genes, such as glyceraldehyde-3-phosphate dehydrogenase (GAPDH) or actin. Other genes (sometimes referred to as "housekeeping" genes) are known in the art.

The information obtained from a comparison of gene expression of NKX2.2 or one or more downstream genes can be used to diagnose Ewing's sarcoma. If NKX2.2 is shown to be expressed at a higher level in the test sample compared to the expression level in the non-cancerous control sample, then it is likely that the sample contains cells of Ewing's sarcoma. Conversely, if NKX2.2 is shown to be expressed at the same or lower level in the test sample compared to the expression level in the non-cancerous control sample, then it is unlikely that the sample contains cells of Ewing's sarcoma.

Compositions and Methods of Treatment of Ewing's Sarcoma

The Ewing's sarcoma markers identified here can serve as targets for therapeutic intervention. Blocking or disrupting the aberrant expression of these marker genes in cancerous cells would prevent or disrupt the ability of Ewing's sarcoma cells to grow or propagate. Thus, aspects of the invention relate to compositions, and methods useful for modulating the expression of genes, such as those genes associated with oncogenesis of Ewing's sarcoma. In some aspects, the present invention includes a composition comprising a therapeutic agent and a pharmaceutically acceptable carrier, wherein the therapeutic agent is present in an effective amount to reduce the expression or activity of NKX2.2 in cancerous cells exposed to the therapeutic agent.

In some embodiments, the therapeutic agent is an agent capable of mediating NKX2.2-specific RNA interference. RNA interference (RNAi) is used to decrease the expression of NKX2.2 in Ewing's sarcoma cells. RNAi refers to the process of sequence-specific post-transcriptional gene silencing in animals mediated by short interfering RNAs (siRNAs) (Zamore et al., 2000, Cell, 101, 25 33; Fire et al., 1998, Nature, 391, 806; Hamilton et al., 1999, Science, 286, 950 951; Lin et al., 1999, Nature, 402, 128 129; Sharp, 1999, Genes & Dev., 13:139 141; and Strauss, 1999, Science, 286, 886). siRNAs are dsRNAs that direct the degradation of their corresponding mRNA targets by an endonuclease complex, commonly referred to as an RNA-induced silencing complex (RISC). The RISC mediates cleavage of single-stranded RNA having sequence complementary to the antisense strand of the siRNA duplex. Cleavage of the target RNA disrupts translation of the mRNA into an active protein, thereby decreasing the overall expression of the gene.

RNAi can be used to interfere with gene expression in mammals. siRNAs may be administered to a cell, thereby initiating the RNAi effect against the target gene in the cell. The siRNAs may comprise any single self-complementary RNA strand or two complementary RNA strands. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition. The RNA molecule may be at least 10, 12, 15, 20, 21, 22, 23, 24, 25, 30, nucleotides in length.

siRNA can be introduced directly into a cell to mediate RNA interference (Elbashir et al., 2001, Nature 411:494 498). Many methods have been developed to make siRNA, e.g, chemical synthesis or in vitro transcription. Once made, the siRNAs are introduced into cells via transient transfection. A number of expression vectors have also been developed to continually express siRNAs in transiently and stably transfected mammalian cells (Brummelkamp et al., 2002 Science 296:550 553; Sui et al., 2002, PNAS 99(6):5515 5520; Paul et al., 2002, Nature Biotechnol. 20:505 508). The vectors may be delivered to a cell using a retrovirus, for example. Some of these vectors have been engineered to express small hairpin RNAs (shRNAs), which get processed in vivo into siRNA-like molecules capable of carrying out gene-specific silencing. Another type of siRNA expression vector encodes the sense and antisense siRNA strands under control of separate pol III promoters (Miyagishi and Taira, 2002, Nature Biotechnol. 20:497 500). The siRNA strands from this vector, like the shRNAs of the other vectors, have 3' thymidine termination signals.

A siRNA molecule can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129 140; Hofland and Huang, 1999, Handb. Exp. Pharmacol., 137, 165 192; and Lee et al., 2000, ACS Symp. Ser., 752, 184 192, all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis (see for example WO 03/043689 and WO 03/030989), or by incorporation into other vehicles, such as biodegradable polymers, hydrogels, cyclodextrins (see for example Gonzalez et al., 1999, Bioconjugate Chem., 10, 1068 1074; Wang et al., International PCT publication Nos. WO 03/47518 and WO 03/46185), poly (lactic-co-glycolic)acid (PLGA) and PLCA microspheres (see for example U.S. Pat. No. 6,447,796 and U.S. Patent Application Publication No. U.S. 2002130430), biodegradable nanocapsules, and bioadhesive microspheres, or by proteinaceous vectors (O'Hare and Normand, International PCT Publication No. WO 00/53722). In another embodiment, the nucleic acid molecules described here can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. Alternatively, the nucleic acid/vehicle combination is locally delivered by direct injection.

RNA containing a nucleotide sequences identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (e.g. BLAST). The length of the identical nucleotide sequences may be at least 10, 15, 20, 25, 50, 100, 200, 300 or 400 bases.

In some aspects, the present provides for therapeutic agents that decrease the activity of the NKX2.2 protein directly or indirectly. Various agents may be used, including: histone deacetylase inhibitors, kinase inhibitors, phosphatase inhibitors, inhibitors of SUMOylation or ubiquitylation, and cyclopamine.

In one embodiment, the activity of the NKX2.2 protein is blocked through the action of a histone deacetylase (HDAC) inhibitor. While not wishing to be bound by theory, it is believed that NKX2.2 recruits HDACs (via its interaction with TLE family members) to "NKX2.2 downstream target" promoters. At these promoters, NKX2.2 sits down, pulls in TLEs, which then pull in HDACs. The HDACs deacetylate the histones at those gene promoters, and cause a repression of gene expression. HDAC inhibitors, then, would prevent NKX2.2 from causing gene repression at these promoters, thereby preventing the oncogenic transcformation of Ewing's sarcoma in these cells. Various histone deacetylase inhibitors may be used in accordance with the present invention including, but not limited to Trichostatin A (TSA), suberoylanilide hydroxamic acid (SAHA, vorinostat), Depsipeptide (FR901228 or FK228), MS-275 (MS-27-275), and CI-994. In a suitable embodiment, where a histone deacetylase inhibitor (e.g. vorinostat) is the therapeutic agent, the daily oral dose may be about 50 to about 500 mg, about to 100 to about 400 mg, or about 200 mg to about 300 mg.

In another embodiment, the activity of NKX2.2 protein may be diminished through the action of cyclopamine (11-deoxojervine). Cyclopamine is naturally-occurring chemical that belongs to the group of steroidal jerveratrum alkaloids. It is a teratogen isolated from the corn lily (*Veratrum californicum*) that can lead to cyclopia (holoprosencephaly). Cyclopamine inhibits the hedgehog signaling pathway (which comprises NKX2.2) by influencing the balance between the active and inactive forms of the Smoothened protein. Thus, compositions comprising cyclopamine as the therapeutic agent may reduce the activity or expression of NKX2.2.

In another embodiment, the activity of NKX2.2 protein may be diminished through the action of a kinase inhibitor. Phosphorylation of serine 164 in NKX2.5 (a closely-related NK2-family member) results in increased DNA binding and transcriptional activity. See Kasahara, H., and S. Izumo. Mol Cell Biol.1999; 19:526-36. The NKX2.5 homeodomain has been shown to be phosphorylated by casein kinase II (CKII) in vivo. The CKII phosphorylation site is perfectly conserved in NKX2.2 (serine 154 in NKX2.2), indicating a role for phosphorylation in modulating NKX2.2 function as well. Thus, action of a kinase inhibitor may decrease the biological activity of NKX2.2. Casein kinase II inhibitors that may be used in accordance with the present invention include, but are not limited to heparin, 2,3-bisphosphoglycerate, acidic polypeptides, 5,6-dibromo-1-(O-D-ribofuranosyl)benzimidazole, and 5,6-dichlorobenzimidazole. In suitable embodiments, heparin is used. Heparin is a potent CKII inhibitor: 5 µg/ml heparin inhibits>90% of the protein kinase activity of CKII.

The therapeutic agents described herein may be administered in a variety of dosage forms. In some aspects, the instant provides for compositions which may be prepared by mixing the therapeutic agents with pharmaceutically acceptable carriers, excipients, binders, diluents or the like to prevent skin cancer. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by topical administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing the therapeutic agent with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

For topical administration, suitable formulations include ointments, creams, gels, lotions, pastes, and the like. Ointments are semisolid preparations that are typically based on petrolatum or other petroleum derivatives. Creams are viscous liquids or semisolid emulsions, either oil-in-water or water-in-oil. Gels are semisolid, suspension-type systems. Lotions are preparations to be applied to the skin surface without friction, and are typically liquid or semiliquid preparations in which solid particles, including the active agent, are present in a water or alcohol base. Lotions are usually suspensions of solids and comprise a liquid oily emulsion of the oil-in-water type. Lotions are preferred formulations herein for treating large body areas, because of the ease of applying a more fluid composition. Pastes are semisolid dosage forms in which the active agent is suspended in a suitable base.

Formulations may also be prepared with liposomes, micelles, and microspheres. Liposomes are microscopic vesicles having a lipid wall comprising a lipid bilayer, and can be used as drug delivery systems. Micelles are known in the art as comprised of surfactant molecules arranged so that their polar head groups form an outer spherical shell, while the hydrophobic, hydrocarbon chains are oriented towards the center of the sphere, forming a core. Microspheres, similarly, may be incorporated into the present formulations and drug delivery systems. Like liposomes and micelles, microspheres essentially encapsulate a drug or drug-containing formulation.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

The formulations of the compositions described herein may be designed to be short-acting, fast-releasing, long-acting, and sustained-releasing as described below. Thus, the pharmaceutical formulations may also be formulated for controlled release or for slow release.

A therapeutically effective dose may vary depending upon the type of therapeutic agent, route of administration, and dosage form. Dosage unit forms generally contain between from about 1 mg to about 500 mg of an active ingredient. The preferred composition or compositions is a formulation that exhibits a high therapeutic index. The therapeutic index is the dose ratio between toxic and therapeutic effects which can be expressed as the ratio between LD50 and ED50. The LD50 is the dose lethal to 50% of the population and the ED50 is the dose therapeutically effective in 50% of the population. The LD50 and ED50 are determined by standard pharmaceutical procedures in animal cell cultures or experimental animals.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation.

In the compositions for treating Ewing's sarcoma described herein, the therapeutically effective amount of the agent can range from about 0.1 mg/kg to about 30 mg/kg body weight of the subject. In some embodiments, the therapeutically effective amount of the agent can range from about 0.5 mg/kg to about 30 mg/kg, from about 1 mg/kg to about 30 mg/kg, from about 1 mg/kg to about 25 mg/kg, from about 1 mg/kg to about 20 mg/kg, or from about 1 or 2 mg/kg to about 15 mg/kg.

Treatment may also include administering the pharmaceutical formulations of the present invention in combination with other therapies. For example, the compounds and pharmaceutical formulations of the present invention may be administered before, during, or after a surgical procedure and/or radiation therapy. The compounds described herein can also be administered in conjunction with other anti-cancer drugs. By anticancer drugs is meant those agents which are used for the treatment of malignancies and cancerous growths by those of skill in the art such as oncologists or other physicians. Thus, anti-cancer drugs and compounds disclosed herein may be administered simultaneously, separately or sequentially. Appropriate combinations and administration regimes can be determined by those of skill in the oncology and medicine arts.

The compounds and formulations described herein are particularly suitable for use in combination therapy as they have been shown or are expected to exhibit an additive or greater than additive or synergistic effect when used in combination with anti-cancer drugs such as taxanes, nitrosoureas, platinum compounds, alkylating agents, topoisomerase I and II inhibitors, vinca alkaloids, anti-cancer antibiotics; interferons, interleukin-2, and radiation treatment.

Screening Methods

In one aspect, the present invention provides methods of screening for therapeutic agents for Ewing's sarcoma. In some methods, the therapeutic agent will show either an effect on the expression of NKX2.2 or one or more NKX2.2 downstream genes or on the activity of NKX2.2 or one or more of the downstream proteins. In some methods, a candidate or test pharmaceutical composition is applied to a cell exhibiting features of Ewing's sarcoma, including, but not limited to: A673 cells, SK-N-MC cells, EWS502 cells, TC71 cells, TC32 cells, or SK-ES-1 cells. Alternatively, the pharmaceutical composition may be applied to a subject having or suspected of having Ewing's sarcoma. Following application of the therapeutic agent, the effect of the agent on the expression of NKX2.2 or one or more NKX2.2 downstream genes is measured. Efficacious candidate pharmaceutical compositions include those which diminish NKX2.2 gene expression or NKX2.2 protein activity or alter the expression of NKX2.2 downstream proteins.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

EXAMPLES

The present methods and compositions, thus generally described, will be understood more readily by reference to the following examples, which are provided by way of illustration and are not intended to be limiting of the present methods and compositions.

Example 1

Experimental Procedures

Constructs and retroviruses: The RNAi retroviral vector pSRP contains an H1 promoter for expression of shRNAs, and a puromycin resistant marker. Oligonucleotide sequences that were cloned downstream of the H1 promoter are provided in Table 1. For some experiments, the puromycin resistance cassette was replaced with a hygromycin resistance cassette. The NKX-RNAi retrovirus used the pMKO.1puro vector (Masutomi et al., 2003). NKX-RNAi sequences are also provided in Table 1.

TABLE 1

RNAi Sequences

| Name | SEQ ID NO | Sequence |
| --- | --- | --- |
| EF-2-RNAiF | SEQ ID NO: 2 | GATCCCCATAGAGGTGGGAAGCTTATTTCAAGAGA ATAAGCTTCCCACCTCTATTTTTTGGAAC |
| EF-2-RNAiR | SEQ ID NO: 3 | TCGAGTTCCAAAAAATAGAGGTGGGAAGCTTATTCT CTTGAAATAAGCTTCCCACCTCTATGGG |
| EF-4-RNAiF | SEQ ID NO: 4 | GATCCCCGACGCCAAGGGCATTGCAGTTCAAGAGA CTGCAATGCCCTTGGCGTCTTTTTGGAAC |
| EF-4-RNAiR | SEQ ID NO: 5 | TCGAGTTCCAAAAAGACGCCAAGGGCATTGCAGTC TCTTGAACTGCAATGCCCTTGGCGTCGGG |
| luc-RNAiF | SEQ ID NO: 6 | GATCCCCCTTACGCTGAGTACTTCGATTCAAGAGAT CGAAGTACTCAGCGTAAGTTTTTGGAAC |

TABLE 1-continued

RNAi Sequences

| Name | SEQ ID NO | Sequence |
|---|---|---|
| luc-RNAiR | SEQ ID NO: X | TCGAGTTCCAAAAACTTACGCTGAGTACTTCGATCTCTTGAATCGAAGTACTCAGCGTAAGGGG |
| ERG-RNAiF | SEQ ID NO: 7 | GATCCCCGACTCTTGGGAGGGAGTTATTCAAGAGATAACTCCCTCCCAAGAGTCTTTTTGGAAAC |
| ERG-RNAiR | SEQ ID NO: 8 | TCGAGTTCCAAAAAGACTCTTGGGAGGGAGTTATCTCTTGAATAACTCCCTCCCAAGAGTCGGG |
| NKX-RNAiF | SEQ ID NO: 9 | CCGGCCATGCCTCTCCTTCTGAAttcaagagaTTCAGAAGGAGAGGCATGGTTTTTG |
| NKX-RNAiR | SEQ ID NO: 10 | AATTCAAAAACCATGCCTCTCCTTCTGAAtctcttgaaTTCAGAAGGAGAGGCATGG |

A FLAG-epitope tagged EWS/FLI cDNA (type 4 breakpoint; May et al., 1993a), or the R2L2 mutant (Bailly et al., 1994), was cloned into the pMSCV-puro retroviral vector (Clontech). A full-length NKX2.2 cDNA was cloned into the retroviral expression vector pQCXIN (Clontech). The inducible EWS/FLI construct, retroviral production and retroviral infection were previously described (Lessnick et al., 2002).

Cell Culture: Ewing's sarcoma cell lines were grown as described (Lessnick et al., 2002). Following retroviral infection, polyclonal cell populations were prepared by growth in the appropriate selective media. Soft agar assays were performed as described (Lessnick et al., 2002). Tet-A673 cells were generated by infection with pREV-TETOFF (Clontech) and selection with G418. A single clone was then infected with FLAG-EWS/FLI-pREV-TRE, and selected with hygromycin in the presence of 1 ug/ml doxycycline and G418 (Lessnick et al., 2002). Individual clones were tested for induction of FLAG-EWS/FLI as previously described (Lessnick et al., 2002).

Xenograft imaging: A673 or TC71 cells were infected with pMMP-LucNeo and selected with G418 (Rubin et al., 2003). They were then infected with either EF-2-RNAi, NKX-RNAi, or ERG-RNAi retroviruses, and selected with puromycin. Following selection, 1×10$^6$ cells were injected into the flanks of nude mice. Mice were imaged weekly using a Xenogen IVIS 100 imaging system, per manufacturer's directions. Animal experiments were performed following approval from the University of Utah Institutional Animal Care and Use Committee.

Northern blot analysis: Positive-control EWS/FLI RNA was prepared using an in vitro transcription reaction. One microgram of mRNA (Ewing's cells), 1 µg of total RNA (Jurkatt cells), or 0.01 µg of in vitro transcribed EWS/FLI RNA were used. Probes for EWS were prepared using PCR to amplify coding bases 1 to 793 (for 5' EWS) or coding bases 802 to 1607 (for 3' EWS). The 5'FLI probe was prepared using PCR to amplify coding bases 44 to 604. The 3'FLI probe was a 475 bp PvuII-HindIII fragment derived from the EWS/FLI cDNA.

Reverse-transcriptase polymerase chain reaction (RT-PCR): Total RNA from the indicated sources was amplified and detected using SYBR green fluorescence for quantitative analysis. For non-quantitative analysis, total RNA was amplified for 35 cycles and the PCR products were subjected to agarose gel electrophoresis. Primer sequences were: forward: CTACGACAGCAGCGACAACC (SEQ ID NO: 13) and reverse: GCCTTGGAGAAAAGCACTCG (SEQ ID NO: 14). Deidentified patient samples were obtained through an approved University of Utah Institutional Review Board Protocol.

Immunodetection: The following antibodies were used for immunodetection: M2-anti-FLAG (Sigma); anti-FLI-1 (BD PharMingen 554266); anti-α-tubulin (Santa Cruz sc-5286); anti-NKX2.2 (Santa Cruz sc-15015).

Microarray analysis: The complete set of microarray data is available on-line at http://www.ncbi.nlm.nih.gov/projects/geo, accession number GSE4565.

Example 2

Transcriptional Signature of EWS/FLI

The gene expression profile of EWS/FLI as it relates to oncogenic transformation was determined. We, and others, have previously shown that significant transcriptional consequences are associated with changes in cell growth (e.g., Lessnick et al., 2002; Zhang et al., 2004). Because A673 cells expressing the EWS/FLI knock-down construct maintain normal growth even though they are no longer transformed (data not shown), there should be minimal contribution of growth effects to the transcriptional profile.

While we have demonstrated that off-target effects do not mediate the loss of transformation observed in A673 cells infected with the EF-2-RNAi retrovirus, off-target effects may still be present (Jackson et al., 2003). To control for this, we identified a second EWS/FLI RNAi construct (designated EF-4-RNAi) that provides significant levels of EWS/FLI knockdown and also disrupts oncogenic transformation (data not shown). We reasoned that different RNAi constructs will have distinct off-target effects, and identification of genes that are altered similarly by both RNAi constructs would control for these.

A673 cells infected with either the EF-2-RNAi or EF-4-RNAi viruses were prepared, in duplicate with their associated controls, and were subjected to microarray analysis. Because these cells were grown in tissue culture for several weeks, these experiments assessed the transcriptional changes that were stably altered by the EWS/FLI fusion. We called these cells "stable-knockdown" cells.

To identify genes that were up- or down-regulated in the presence of the EWS/FLI RNAi constructs, we sorted genes using the signal-to-noise metric followed by permutation testing. We found that EWS/FLI upregulated 320 genes, and downregulated 1151 genes at the 95% confidence level (FIG. 1A). The fact that EWS/FLI downregulated so many more genes than it upregulated was counterintuitive since prior work (performed in murine fibroblasts) suggested that EWS/FLI functions as a transcriptional activator to mediate oncogenic transformation (Lessnick et al., 1995; May et al., 1993b).

The "stable-knockdown" results are likely to include both direct and indirect EWS/FLI target genes. To determine which genes are directly regulated by EWS/FLI, we attempted to perform chromatin immunoprecipitation experiments. Unfortunately, we found unacceptably high levels of background immunoprecipitation with commercially-available EWS/FLI antibodies, and were unable to adequately complete these experiments.

As an alternate approach, we used an "inducible-rescue" experiment to enrich for genes that are likely to be direct EWS/FLI targets. Endogenous EWS/FLI was knocked-down with the EF-2-RNAi retrovirus in Tet-A673 cells. The exogenous EWS/FLI cDNA was then induced, and samples were collected at various times after induction, processed, and hybridized to oligonucleotide microarrays.

Induction of the exogenous EWS/FLI transcript was monitored with the 211825_s_at probe set. We identified 1326 genes with expression changes of at least 2.5 fold, and rank-ordered these based on similarity of expression to the induced exogenous EWS/FLI transcript using the Pearson correlation coefficient as the distance metric (FIG. 1B).

To compare the "stable-knockdown" and "inducible-rescue" experiments, we performed a modified gene set enrichment analysis (GSEA; Mootha et al., 2003). We first identified the most reproducibly-altered genes in the "stable-knockdown" A673 cells described above. Using a 2.5 fold change cut-off value, we identified 33 genes that were upregulated, and 180 genes that were downregulated by EWS/FLI in each of the four replicates (see FIG. 1A). We then compared these to the 1326 rank-ordered genes from the "inducible-rescue" cells.

If the two datasets are well-correlated, we expect the EWS/FLI regulated genes in the stable-knockdown experiment to be enriched at the top of the rank-ordered list from the inducible-rescue experiment. This correlation was quantified using a normalized running sum statistic called the normalized enrichment score (NES). The maximal and minimal NES were determined. The best possible NES is 100 (indicating perfect correlation), and the worst possible NES is –100 (indicating perfect inverse correlation). An empiric p-value was derived based on the number of times a maximal NES (or minimal NES) was obtained from 10,000 randomly-chosen genesets that was the same, or greater than, the experimentally-determined value. Additional details are presented in the supplemental materials.

Comparison of the 33 EWS/FLI upregulated genes to the inducible-rescue experiment yielded a maximal NES of 80.3 (p<0.0001), indicating excellent correlation (FIG. 1C). Comparison of the 180 EWS/FLI downregulated genes to the inducible-rescue experiment gave a minimal NES of –72.4 (p<0.0001), indicating a highly significant inverse correlation as one would expect for downregulated genes (FIG. 1D). Thus, the results from the stable-knockdown and inducible-rescue experiments are highly similar. We therefore conclude that the vast majority of EWS/FLI regulated genes are regulated in the same time frame as EWS/FLI, suggesting that many of these are likely to be direct EWS/FLI target genes.

To validate the microarray data using an alternate technique, and to extend the results to other Ewing's sarcoma cell lines, we performed quantitative RT-PCR (qRT-PCR) analyses on a random set of genes from FIG. 1C. EWS/FLI was knocked down in A673, SK-N-MC, and EWS-502 Ewing's sarcoma cells with the EF-2-RNAi retrovirus. Amplification of each gene was compared in these cells to control cells expressing the luc-RNAi control. We found that knockdown of EWS/FLI resulted in similar decreases in each gene tested (Table 2). These results confirm the initial microarray data, and suggest that EWS/FLI regulates similar genes in other Ewing's sarcoma cell lines as well.

TABLE 2

Microarray Validation by qRT-PCR

| | A673 | SK-N-MC | EWS502 |
|---|---|---|---|
| EWS/FLI | 74% (p = 0.02) | 57% (p = 0.005) | 68% (p = 0.02) |
| FCGRT | 94% (p = 0.002) | 67% (p = 0.0006) | 85% (p = 0.0006) |
| CNTNAP2 | 86% (p = 0.01) | 49% (p = 0.03) | 63% (p = 0.02) |
| GSTM4 | 80% (p = 0.0002) | 62% (p = 0.01) | 77% (p = 0.02) |
| NKX2.2 | 84% (p = 0.02) | 57% (p = 0.0007) | 52% (p = 0.0009) |
| PPP1R1A | 92% (p = 0.01) | 87% (p = 0.002) | 79% (p = 0.04) |

Inspection of the data revealed that EWS/FLI upregulated multiple genes related to neural differentiation, consistent with the neural-crest phenotype of Ewing's sarcoma tumors. These included NKX2.2, NPY1R, RET, EPHB3, DAB 1, CDH12, and CNTNAP2. These data support the previous assertion that EWS/FLI itself induces the neural phenotype of Ewing's sarcoma, rather than the phenotype occurring as a consequence of the tumor's cell of origin (Teitell et al., 1999).

Identification of SSX family members (which are fused to SYT in synovial sarcoma, another sarcoma of uncertain origin) suggests the potential for common mechanisms of oncogenic transformation across the fusion-associated solid tumors of adolescents and young adults. The upregulation of GYG2, which can nucleate the initial step of glycogen formation through autoglucosylation, suggests a molecular mechanism for the high levels of glycogen observed in Ewing's sarcoma (Mu et al., 1997; Navas-Palacios et al., 1984). We also identified upregulation of the SH2D1A gene, which encodes an SH2-domain-only protein that is highly similar to EAT2, which has been previously identified as an EWS/FLI target gene (Braun et al., 1995). EAT2 itself was not represented on the microarray used.

With respect to other previously identified EWS/FLI target genes, TGFBR2 was repressed by EWS/FLI, as previously reported (Hahm et al., 1999). MYC, ID2, MFNG, KRT15, UBE2C, CYP2F1, and CDKN1C were not significantly altered (Arvand et al., 1998; Bailly et al., 1994; Dauphinot et al., 2001; Fukuma et al., 2003; May et al., 1997). Uridine-phosphorylase (UPP 1), MMP3 (stromelysin 1), and PDGFC were downregulated, rather than upregulated as previously reported (Braun et al., 1995; Deneen et al., 2003, Zwemer and May, 2001). It should be noted that many of these were identified in alternate models of EWS/FLI expression (e.g., in NIH3T3 cells) rather than in Ewing's sarcoma itself.

To extend the analysis of previously-reported EWS/FLI target genes beyond those listed above, we compared the microarray data we obtained in A673 Ewing's sarcoma cells to publicly-available data generated in two alternate systems: human rhabdomyosarcoma cells and primary human fibroblasts expressing inducible EWS/FLI protein (RD-EF and tet-EF, respectively; Hu-Lieskovan et al., 2005b; Lessnick et al., 2002). The list of EWS/FLI upregulated genes in each dataset was compared to the EWS/FLI upregulated genes in both the stable-knockdown and the inducible-rescue A673 cells using Chi square analysis. We found small but highly significant overlaps between EWS/FLI-regulated genes in both of these heterologous models and the A673 systems (Table 3). Thus, the A673 system identified genes which were found in other EWS/FLI model systems, supporting the validity of our model. The A673 model also identified many genes that were not observed in these heterologous systems, thus demonstrating the importance of this model.

TABLE 3

Comparison of EWS/FLI Gene Datasets

|  | RD-EF | Tet-EF |
|---|---|---|
| A673 stable-knockdown | $5.2 \times 10^{-4}$ | $1.5 \times 10^{-3}$ |
| A673 inducible-rescue | $2 \times 10^{-8}$ | $1.4 \times 10^{-4}$ |

Example 3

Comparison of EWS/FLI Signatures to Ewing's Sarcoma

Ewing's sarcoma is highly associated with the EWS/FLI oncoprotein. If the genes we identified are valid targets, they should also be expressed in Ewing's sarcoma, but not in other pediatric tumors. To test this, we compared our data with publicly-available microarray data on small round blue cell tumors of childhood (SRBCT; Khan et al., 2001), which included Ewing's sarcoma. The genes in the SRBCT dataset were sorted to distinguish between Ewing's sarcoma and the other tumors, using the signal-to-noise metric as a distance measure (Lessnick et al., 2002). The datasets were mapped to their UniGene identifiers to allow for comparisons between different microarray platforms.

The stable-knockdown and inducible-rescue rank-ordered lists were compared to the SRBCT list using the Spearman correlation coefficient (Table 4). When used in this way, the Spearman coefficient quantifies the correlation of gene rank position between datasets. An empiric p-value was derived by repeatedly shuffling the rank-order of one of the two datasets in a pair, and determining the number of times that a correlation coefficient was obtained that was higher than the experimentally-determined coefficient.

TABLE 4

Correlation of Gene Rank Position Between Datasets

| SRBCT versus | Spearman correlation coefficient | p-value | number of common genes |
|---|---|---|---|
| A673 stable knockdown | 0.30 | <0.0001 | 313 |
| A673 inducible-rescue | 0.43 | <0.0001 | 209 |

While both of our datasets showed significant similarity to the human tumor dataset, the inducible-rescue data were more closely correlated to the human tumor data than the stable-knockdown data, with a Spearman correlation coefficient of 0.43 versus 0.30, respectively (table 4). These values were highly statistically significant, with p values of <0.0001 for each. Thus, the inducible-rescue data more accurately identified Ewing's sarcoma-specific genes than the stable-knockdown data.

Example 4

NKX2.2 is Required for Oncogenic Transformation

Because loss of EWS/FLI results in loss of transformation, EWS/FLI-regulated genes should include those required for Ewing's sarcoma development. Because prior data suggested that transcriptional activation is critical to the function of EWS/FLI as an oncoprotein, we focused our efforts on genes that were upregulated by the fusion (FIG. 1C). Using an RNAi approach to analyze the oncogenic role of candidate genes, we identified NKX2.2 as a critical mediator of transformation mediated by EWS/FLI (see below).

Figure 2:
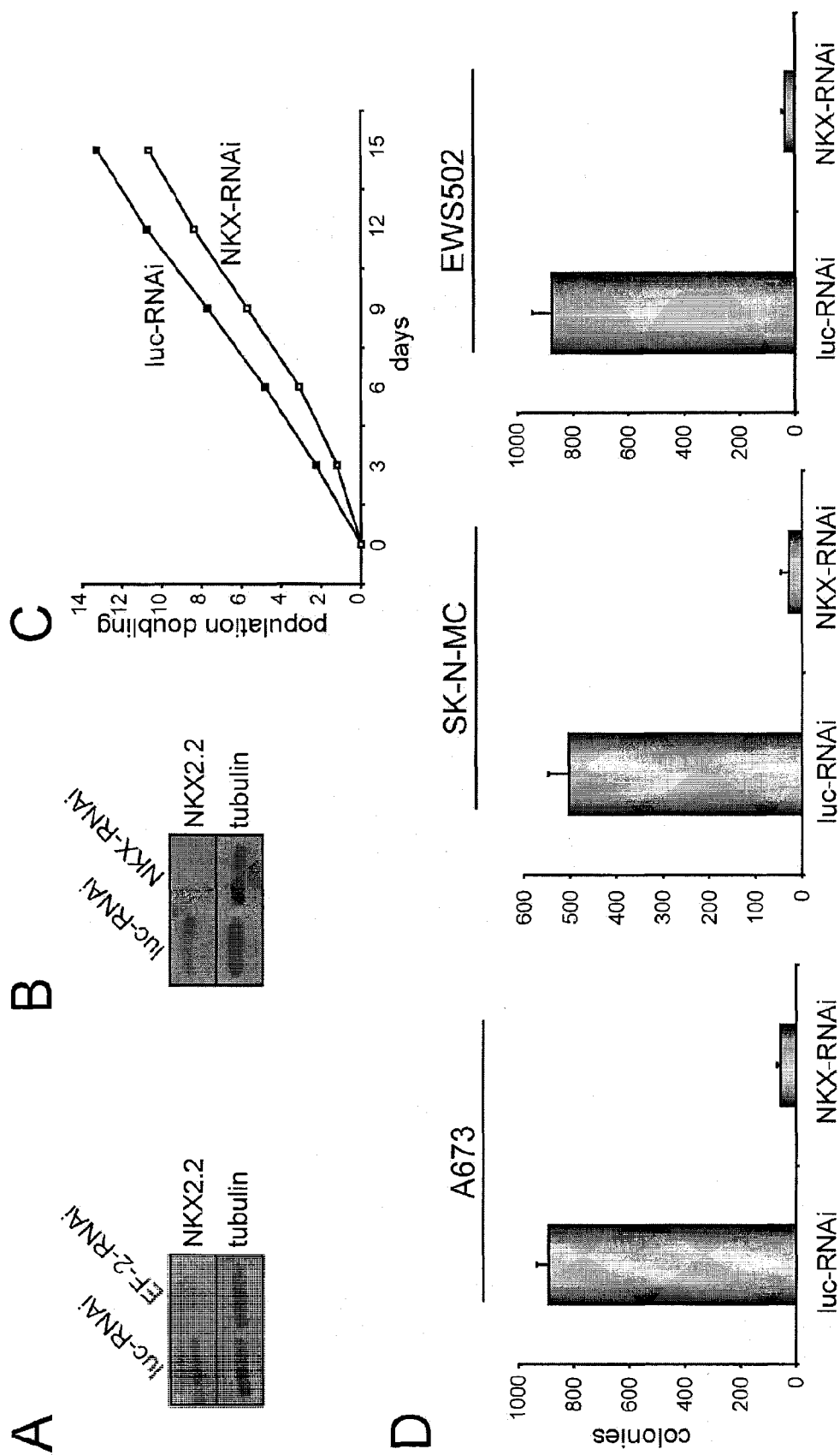
FIG. 2 presents data showing that NKX2.2 is a critical EWS/FLI target gene required for oncogenesis.
Figure 2:
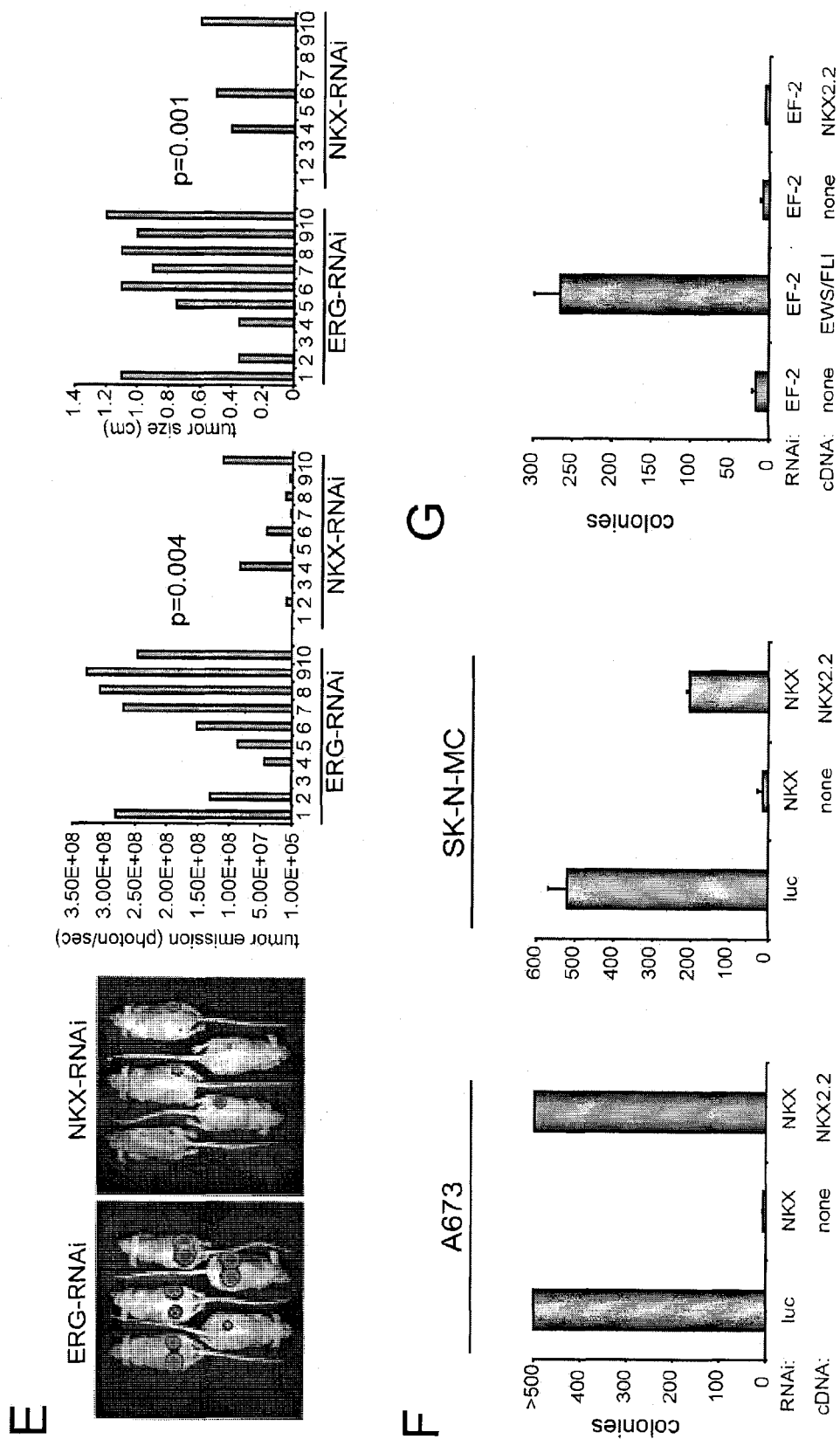

NKX2.2 is a homeobox containing-protein that has roles in neuronal development, but has never been implicated as having a role in tumorigenesis (Briscoe et al., 1999). As shown in Table 2, NKX2.2 transcript levels are regulated by EWS/FLI in multiple Ewing's sarcoma cell lines. NKX2.2 protein is also decreased following knockdown of EWS/FLI in multiple Ewing's sarcoma cell lines (FIG. 2A and data not shown). Thus, NKX2.2 is an EWS/FLI target in multiple Ewing's sarcoma cell lines, although whether it is directly, or indirectly, regulated by EWS/FLI remains to be determined.

We developed a retroviral NKX2.2 RNAi construct (designated NKX-RNAi), and introduced it into A673 Ewing's sarcoma cells. This construct targets a sequence on NKX2.2 according to: CCATGCCTCTCCTTCTGAA (SEQ ID NO: 12). This construct resulted in a 73% reduction of endogenous NKX2.2 transcript levels (data not shown), which is similar to the 84% reduction of NKX2.2 transcript levels following EWS/FLI knockdown. NKX2.2 protein levels were similarly reduced by NKX-RNAi (FIG. 2B).

Introduction of NKX-RNAi into multiple Ewing's sarcoma cells resulted in a near complete loss of oncogenic transformation both in soft agar assays (FIG. 2D), and in a xenograft model of Ewing's sarcoma (FIG. 2E). Transformation was rescued when NKX2.2 was re-expressed using a cDNA that does not contain the endogenous 3' UTR, and so is unaffected by the RNAi (FIG. 2F). Taken together, these data show that NKX2.2 is necessary for oncogenic transformation in Ewing's sarcoma.

To determine if NKX2.2 is sufficient for transformation, we knocked down EWS/FLI with the EF-2-RNAi retrovirus, and reintroduced NKX2.2 expression from the cDNA-containing retroviral vector. We found that NKX2.2 could not rescue the loss of transformation resulting from EWS/FLI knockdown (FIG. 2G). We also found that NKX2.2 did not induce oncogenic transformation in NIH3T3 murine fibroblasts (data not shown). Thus, although NKX2.2 is necessary for oncogenic transformation in Ewing's sarcoma, it is not sufficient.

Figure 3:
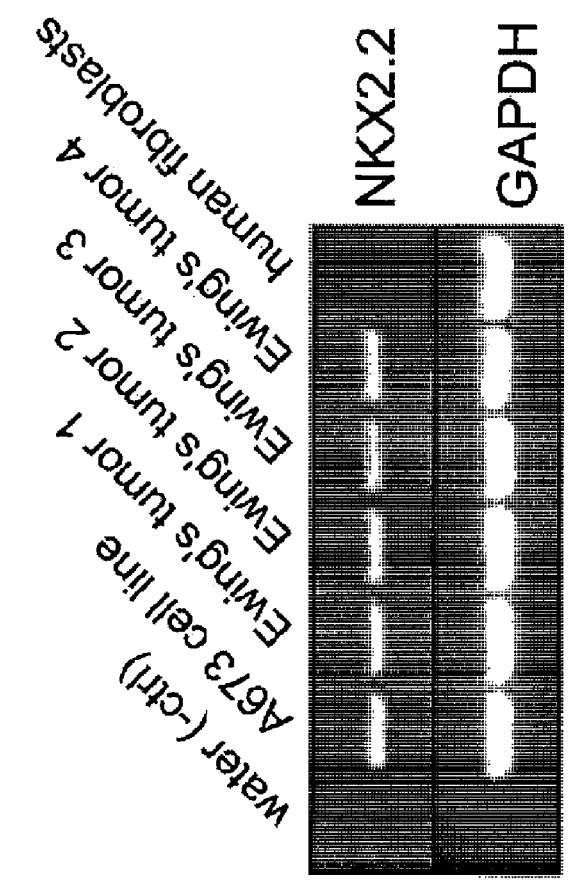
FIG. 3 presents data showing that NKX2.2 is expressed in Ewing's sarcoma tumor samples.
Figure 3:
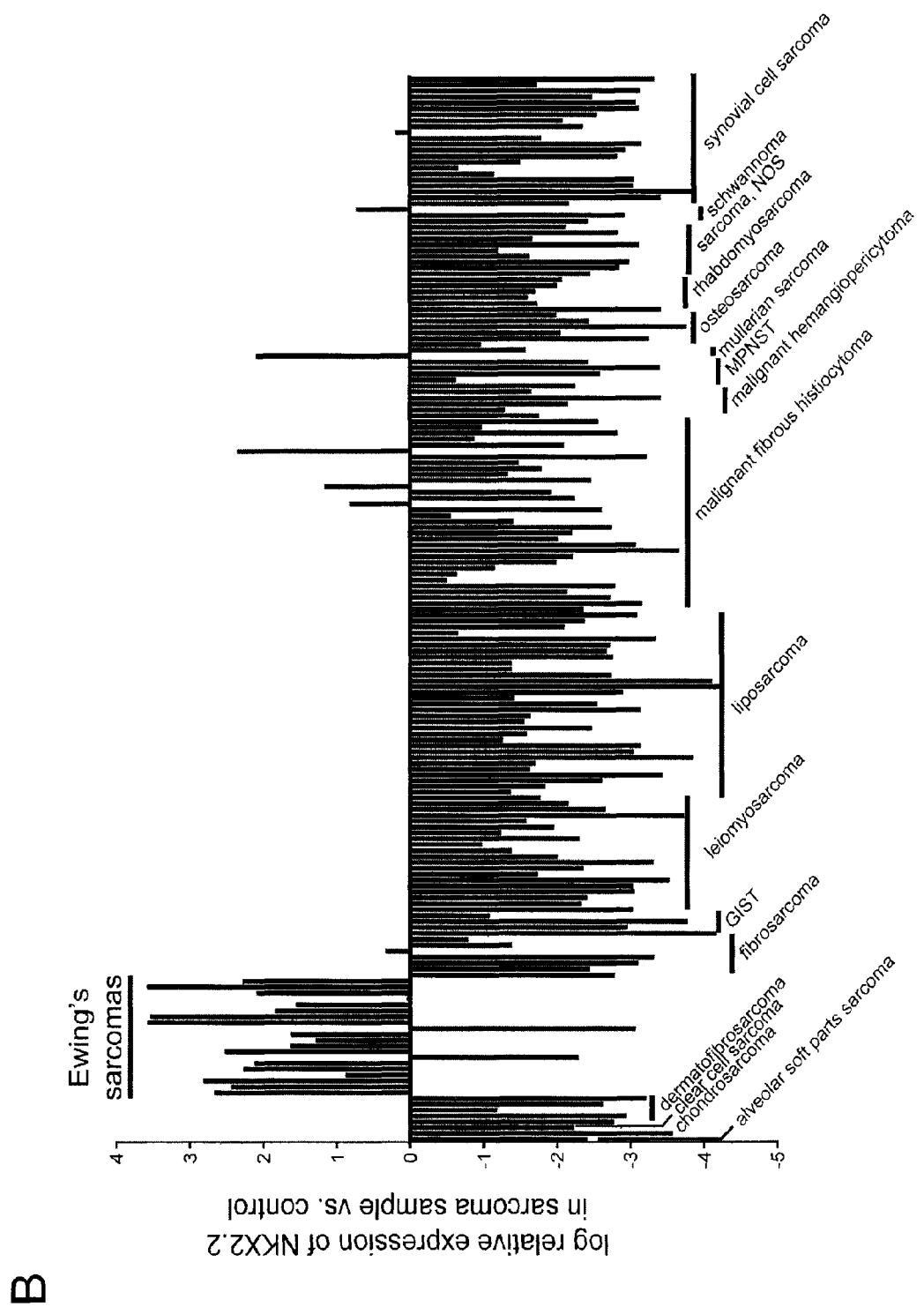

We reasoned that if NKX2.2 were a critical EWS/FLI target gene, then it should be expressed in patient-derived primary Ewing's sarcoma tumor samples as well. We performed RT-PCR for NKX2.2 in four Ewing's sarcoma tumor samples. NKX2.2 was expressed in each of the tumor samples, but not in normal human fibroblasts (FIG. 3A). We then analyzed the expression pattern of NKX2.2 in a recently published microarray dataset containing 181 sarcoma tumor samples, including 20 Ewing's sarcomas (Baird et al., 2005). NKX2.2 was expressed in most (18 of 20) Ewing's sarcoma samples, but was expressed in only 7 of 161 of the other tumors (FIG. 3B). In this dataset, then, NKX2.2 is an excellent marker of Ewing's sarcoma, with a sensitivity of 90%, and a specificity of 96%. These data support the assertion that NKX2.2 is a critical EWS/FLI target gene required for oncogenic transformation in Ewing's sarcoma, and also suggest that NKX2.2 may serve as a new diagnostic marker for this disease.

Example 5

Immunohistochemical Detection of NKX2.2

Figure 4:
FIG. 4 presents data showing immunohistochemical staining of NKX2.2 in Ewing's sarcoma cells.

The anti-NKX2.2 antibody (Santa Cruz sc-15015) was used for immunohistochemical detection of NKX2.2 in A673 cells. The results are shown in FIG. 4 and indicate that NKX2.2 can be detected using immunohistochemistry in Ewing's sarcoma cells. Based on the fact that NKX2.2 is a transcription factor, one expects to find it in the nucleus. Thus, appropriate staining for NKX2.2 is demonstrated by the presence of nuclear staining of the tumor specimen.

Example 6

Effects of NKX2.2 Knockdown on Ewing's Sarcoma Cell Growth

Figure 5A:
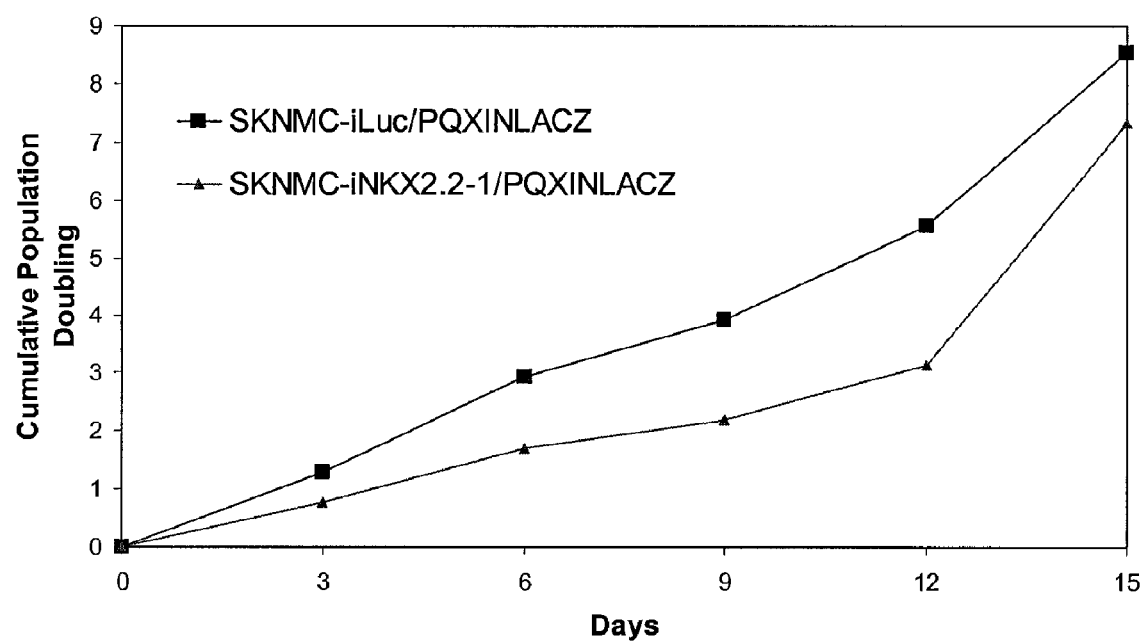
FIG. 5 presents data showing the effect of NKX2.2 knockdown on the growth of Ewing's sarcoma in various cell lines using the shRNA iNKX2.2.
Figure 5B:
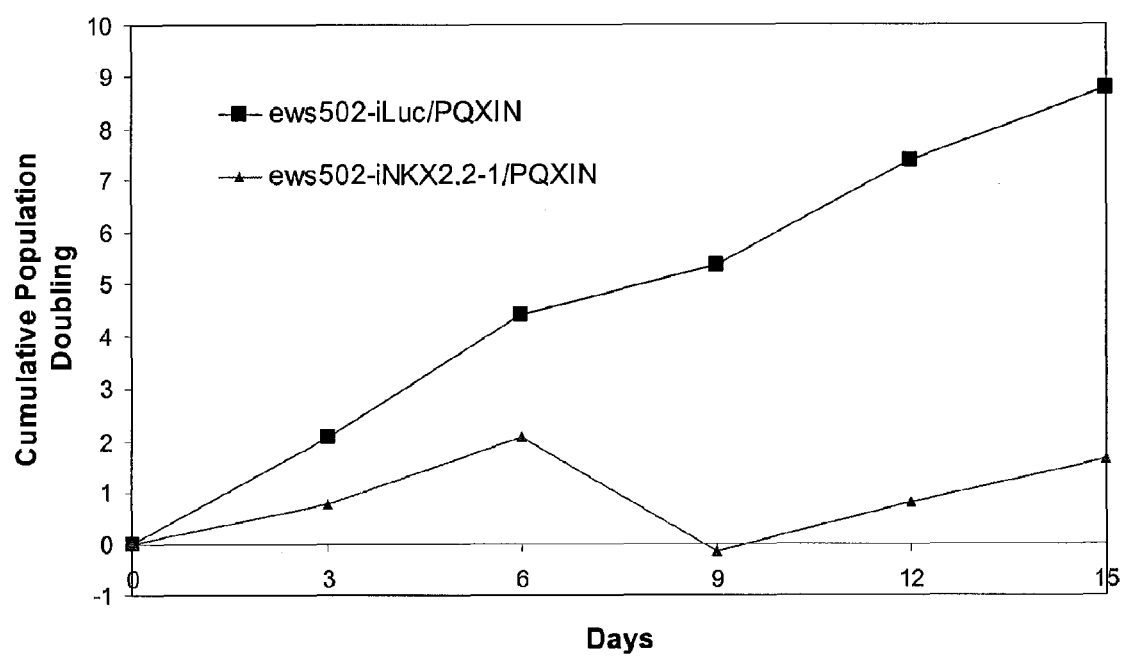
Figure 5C:
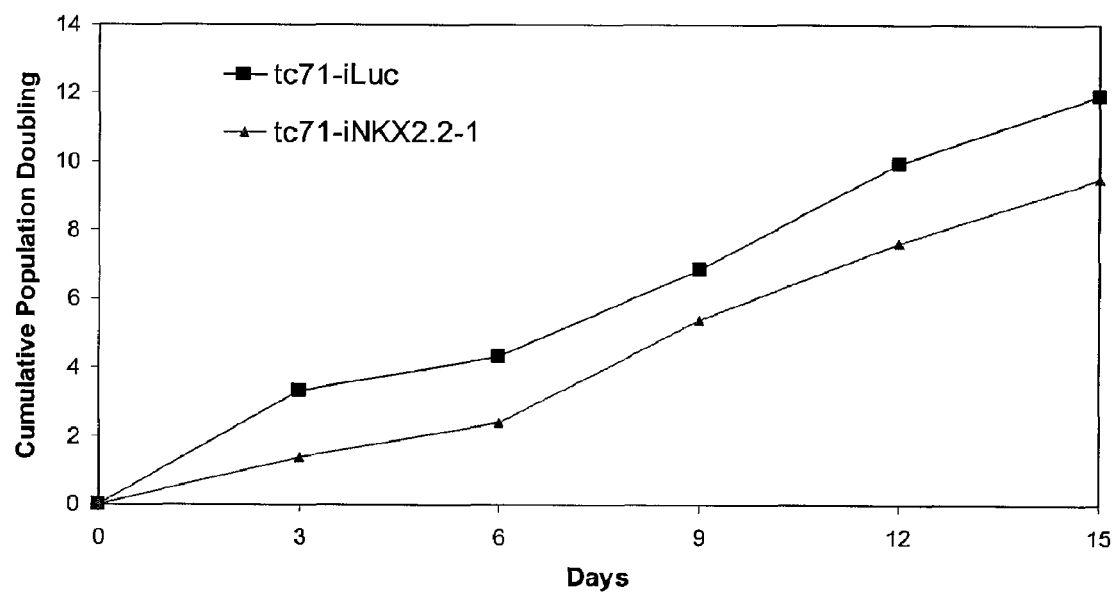
Figure 5D:
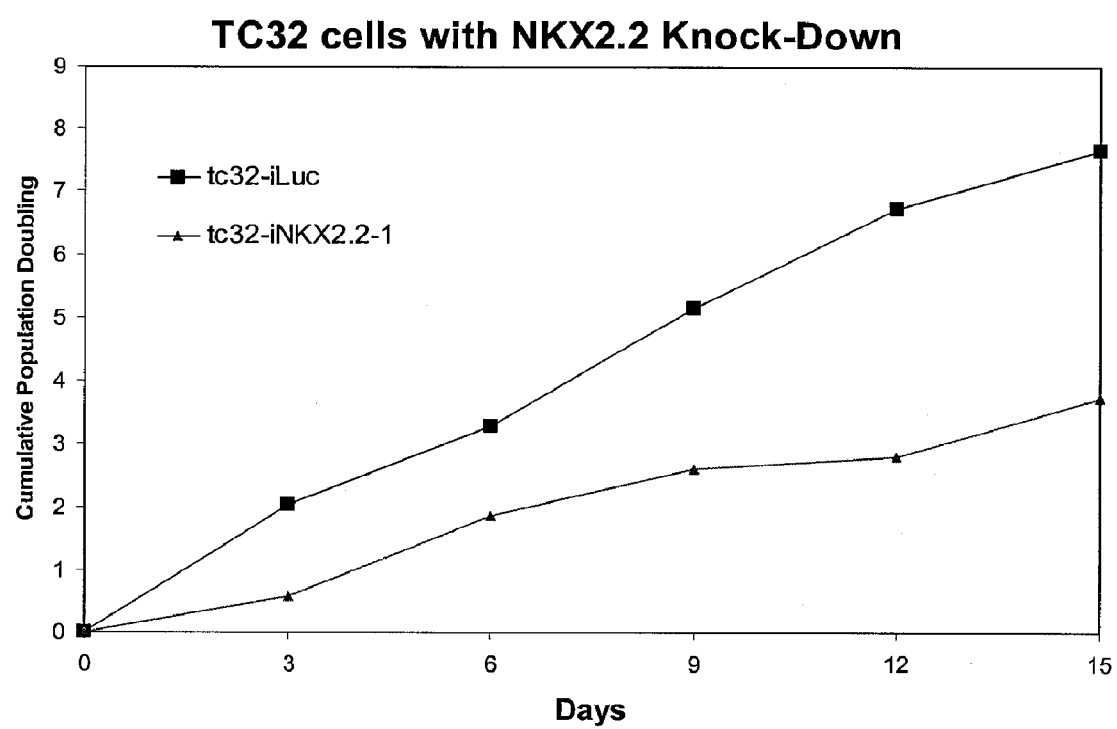

Knockdown of NKX2.2 was performed using the RNAi construct discussed above (targeting the sequence of NKX2.2 corresponding to SEQ ID NO: 12). Loss of NKX2.2 had minimal effects on the growth rate of A673 Ewing's sarcoma cells (FIG. 2C), however, significant effects were observed in other cell lines compared to cells transformed with the iLuc construct (FIG. 5). Thus, significant inhibition was observed with NKX2.2 knockdown in cell lines SK-N-MC (FIG. 5A), EWS502 (FIG. 5B), TC71 (FIG. 5C), and TC32 (FIG. 5D).

Example 7

Histone Deacetylase Inhibitor Blocks Transformation of Ewing's Sarcoma Cells

Figure 6:
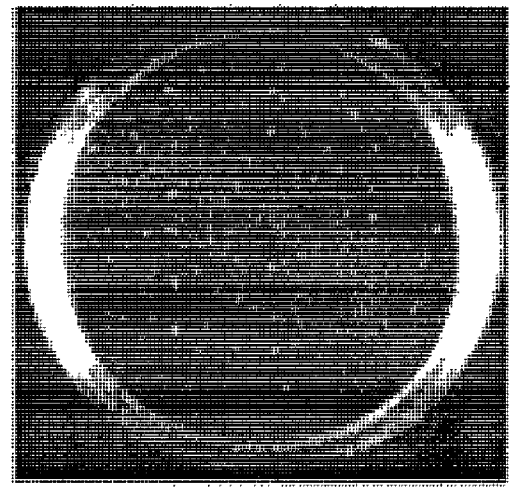
FIG. 6 presents data showing the effect of the histone deacetylase inhibitor, TSA on the growth of A673 Ewing's sarcoma cells.
Figure 6:
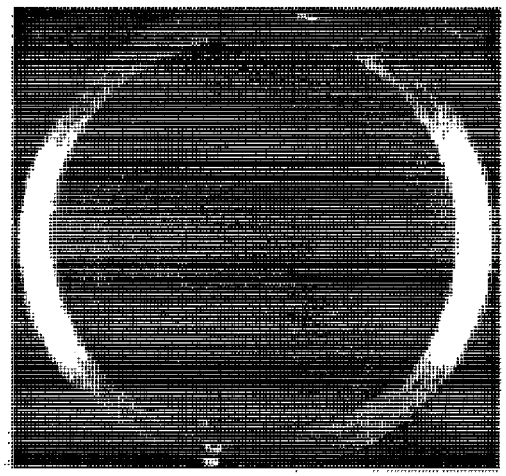

To test the effect of a histone deacetylase inhibitor on NKX2.2 activity, A673 Ewing's sarcoma cells were seeded into soft agar in the presence of 1.5 uM tricostatin (TSA), or ethanol (the TSA carrier) (FIG. 6). The results indicate that the presence of TSA prevents Ewing's cells from forming colonies in soft agar. Soft agar colony formation is one measure of oncogenic transformation. Thus, the histone deacetylase inhibitor TSA blocks oncogenic transformation of Ewing's sarcoma cells.

Example 8

Identification of NKX2.2 Regulated Genes

To identify NKX2.2 downstream target genes, we developed a retroviral RNAi construct that targets the 3' UTR of NKX2.2 in the pMK0.1P retroviral vector (called NKX-RNAi, see above). Infection of this retrovirus into Ewing's sarcoma cells results in efficient knock-down of NKX2.2. Cells were prepared in which NKX2.2 was knocked down using this construct. Control cells were prepared in which a luciferase-directed RNAi construct (luc-RNAi) was introduced (luciferase was not expressed in these cells). Additionally, cells in which NKX2.2 was knocked down with the NKX-RNAi construct were "rescued" with either an empty retroviral vector (as a control), or with an NKX2.2 cDNA that did not contain its 3'UTR (and was thus unaffected by the NKX-RNAi construct). Each set of cells was prepared in duplicate or triplicate. Following infection and selection in the appropriate selectable marker, cells were recovered, RNA isolated, and prepared and hybridized to Affymetrix U133plus2 oligonucleotide microarrays. Data was collected on an Affymetrix scanner.

Data was processed using the MAS5 algorhythm (from Affymetrix), and normalized. The signal-to-noise metric was used to identify genes whose expression was altered in parallel to the presence, or absence, of NKX2.2 expression (i.e., we identified genes whose expression went up, or down, when NKX2.2 was knocked-down, etc.). We used permuation testing to identify genes which were significant at the $p<0.01$ level. Using this approach, we identified 159 genes which were downregulated by NKX2.2, and no genes that were upregulated by the protein (Table 5).

TABLE 5

NKX2.2 Target Genes

| NKX2.2 Target | Annotation |
|---|---|
| FBLN5 | Fibulin 5 |
| LOX | Lysyl oxidase |
| KIAA1530 | KIAA1530 protein |
| Hs.7911 | |
| PAG | Phosphoprotein associated with glycosphingolipid microdomains 1 |
| ZNF217 | Zinc finger protein 217 |
| COL1A2 | Collagen, type I, alpha 2 |
| MAZ | MYC-associated zinc finger protein (purine-binding transcription factor) |
| PDE4DIP | Phosphodiesterase 4D interacting protein (myomegalin) |
| COX4I1 | Cytochrome c oxidase subunit IV isoform 1 |
| EMCN | Endomucin |
| NFKBIZ | Nuclear factor of kappa light polypeptide gene enhancer in B-cells inhibitor, zeta |
| ABAT | 4-aminobutyrate aminotransferase |
| FOXO1A | Forkhead box O1A (rhabdomyosarcoma) |
| RAB40B | RAB40B, member RAS oncogene family |
| ANAPC5 | Anaphase promoting complex subunit 5 |
| TPP1 | Tripeptidyl peptidase I |
| WBP1 | WW domain binding protein 1 |
| HPS1 | Hermansky-Pudlak syndrome 1 |
| FLJ12604 | Ventricular zone expressed PH domain homolog 1 (zebrafish) |
| CHES1 | Checkpoint suppressor 1 |
| SULT1E1 | Sulfotransferase family 1E, estrogen-preferring, member 1 |
| LOX | Lysyl oxidase |
| APOE | Apolipoprotein E |
| FAP | Fibroblast activation protein, alpha |
| COL3A1 | Collagen, type III, alpha 1 (Ehlers-Danlos syndrome type IV, autosomal dominant) |
| MARCKS | Myristoylated alanine-rich protein kinase C substrate |
| TGFBI | Transforming growth factor, beta-induced, 68 kDa |

TABLE 5-continued

NKX2.2 Target Genes

| NKX2.2 Target | Annotation |
|---|---|
| FLJ10579 | Family with sequence similarity 82, member C |
| SLC10A4 | Solute carrier family 10 (sodium/bile acid cotransporter family), member 4 |
| ABAT | 4-aminobutyrate aminotransferase |
| FLJ25756 | Hypothetical protein FLJ25756 |
| RUNX1T1 | Runt-related transcription factor 1translocated to, 1 (cyclin D-related) |
| CXCR4 | Chemokine (C—X—C motif) receptor 4 |
| Hs.403972 | |
| CLIPR-59 | CLIP-170-related protein |
| SOX12 | SRY (sex determining region Y)-box 12 |
| POSTN | Periostin, osteoblast specific factor |
| FIBL-6 | Hemicentin 1 |
| Hs.153368 | |
| FLJ38451 | FLJ38451 protein |
| GAP43 | Growth associated protein 43 |
| ARID2 | AT rich interactive domain 2 (ARID, RFX-like) |
| FANCA | Fanconi anemia, complementation group A |
| Hs.376281 | |
| PI15 | Peptidase inhibitor 15 |
| MYO9A | Myosin IXA |
| SEPP1 | Selenoprotein P, plasma, 1 |
| MGC15476 | Thymus expressed gene 3-like |
| C21orf58 | Chromosome 21 open reading frame 58 |
| CD24 | CD24 antigen (small cell lung carcinoma cluster 4 antigen) |
| COL3A1 | Collagen, type III, alpha 1 (Ehlers-Danlos syndrome type IV, autosomal dominant) |
| TCF7L2 | Transcription factor 7-like 2 (T-cell specific, HMG-box) |
| Hs.97341 | |
| TAGLN | Transgelin |
| CYR61 | Cysteine-rich, angiogenic inducer, 61 |
| ZNF25 | Zinc finger protein 25 (KOX 19) |
| SYN1 | Synapsin I |
| FLJ38507 | Vestigial-like 3 |
| ANAPC5 | Anaphase promoting complex subunit 5 |
| Hs.452398 | |
| C6orf155 | Chromosome 6 open reading frame 155 |
| RANBP1 | RAN binding protein 1 |
| FBP1 | Fructose-1,6-bisphosphatase 1 |
| BTBD9 | BTB (POZ) domain containing 9 |
| ACTG2 | Actin, gamma 2, smooth muscle, enteric |
| ANTXR2 | Anthrax toxin receptor 2 |
| PLXDC1 | Plexin domain containing 1 |
| SLITRK6 | SLIT and NTRK-like family, member 6 |
| ZNF333 | Zinc finger protein 333 |
| Hs.445169 | |
| ATP6V0E | ATPase, H+ transporting, lysosomal 9 kDa, V0 subunit e |
| Hs.4224 | |
| COL3A1 | Collagen, type III, alpha 1 (Ehlers-Danlos syndrome type IV, autosomal dominant) |
| Hs.535610 | |
| Hs.441073 | |
| CD24 | CD24 antigen (small cell lung carcinoma cluster 4 antigen) |
| FLJ37131 | Chromosome 8 open reading frame 31 |
| NEFL | Neurofilament, light polypeptide 68 kDa |
| CCNG2 | Cyclin G2 |
| Hs.464819 | |
| MGC27165 | Hypothetical protein MGC27165 |
| DCAMKL1 | Doublecortin and CaM kinase-like 1 |
| CDH6 | Cadherin 6, type 2, K-cadherin (fetal kidney) |
| Hs.384594 | |
| CLSTN3 | Calsyntenin 3 |
| TAGLN | Transgelin |
| ALOX12 | Arachidonate 12-lipoxygenase |
| Hs.59908 | |
| ATXN1 | Ataxin 1 |
| PDGFRB | Platelet-derived growth factor receptor, beta polypeptide |
| PCOLCE | Procollagen C-endopeptidase enhancer |
| RAB27A | RAB27A, member RAS oncogene family |
| NPAS2 | Neuronal PAS domain protein 2 |
| ZNF505 | Zinc finger protein 505 |
| MYH7B | Myosin, heavy polypeptide 7B, cardiac muscle, beta |
| Hs.543737 | |
| Hs.533025 | |
| MGC1203 | Coiled-coil domain containing 28B |
| STIM1 | Stromal interaction molecule 1 |
| P2RY1 | Purinergic receptor P2Y, G-protein coupled, 1 |
| OLFM3 | Olfactomedin 3 |

TABLE 5-continued

NKX2.2 Target Genes

| NKX2.2 Target | Annotation |
|---|---|
| COL12A1 | Collagen, type XII, alpha 1 |
| KIAA1841 | KIAA1841 protein |
| C6orf155 | Chromosome 6 open reading frame 155 |
| MPP5 | Membrane protein, palmitoylated 5 (MAGUK p55 subfamily member 5) |
| NAP1L4 | Nucleosome assembly protein 1-like 4 |
| TMF1 | TATA element modulatory factor 1 |
| GPSN2 | Glycoprotein, synaptic 2 |
| Hs.551138 | |
| MYO1G | Myosin IG |
| TTLL1 | Tubulin tyrosine ligase-like family, member 1 |
| PBOV1 | Prostate and breast cancer overexpressed 1 |
| DOCK1 | Dedicator of cytokinesis 1 |
| Hs.112899 | |
| LOC124402 | LOC124402 |
| DCHS1 | Dachsous 1 (*Drosophila*) |
| PLUNC | Palate, lung and nasal epithelium carcinoma associated |
| ANKRD12 | Ankyrin repeat domain 12 |
| BMP7 | Bone morphogenetic protein 7 (osteogenic protein 1) |
| MALAT1 | Metastasis associated lung adenocarcinoma transcript 1 (non-coding RNA) |
| DFNB31 | Deafness, autosomal recessive 31 |
| Hs.510685 | |
| SYN2 | Synapsin II |
| PPAP2A | Phosphatidic acid phosphatase type 2A |
| C20orf112 | Chromosome 20 open reading frame 112 |
| DZIP3 | Zinc finger DAZ interacting protein 3 |
| LOC285989 | Hypothetical protein LOC285989 |
| FLJ30594 | Hypothetical locus FLJ30594 |
| FAM43A | Family with sequence similarity 43, member A |
| MCAM | Melanoma cell adhesion molecule |
| FLJ21963 | FLJ21963 protein |
| LZTS2 | Leucine zipper, putative tumor suppressor 2 |
| MGC13017 | Similar to RIKEN cDNA A430101B06 gene |
| PPM2C | Protein phosphatase 2C, magnesium-dependent, catalytic subunit |
| SELM | Selenoprotein M |
| AKAP8L | A kinase (PRKA) anchor protein 8-like |
| Hs.460107 | |
| COL1A2 | Collagen, type I, alpha 2 |
| NY-REN-58 | NY-REN-58 antigen |
| Hs.527697 | |
| C20orf102 | Chromosome 20 open reading frame 102 |
| TMEFF1 | Transmembrane protein with EGF-like and two follistatin-like domains 1 |
| ANKRD12 | Ankyrin repeat domain 12 |
| LEPREL2 | Leprecan-like 2 |
| MGC50559 | Hypothetical protein MGC50559 |
| KIAA0644 | KIAA0644 gene product |
| ZNF324 | Zinc finger protein 324 |
| CTHRC1 | Collagen triple helix repeat containing 1 |
| KIAA0644 | KIAA0644 gene product |
| Hs.553504 | |
| FBXO15 | F-box protein 15 |
| RAB3B | RAB3B, member RAS oncogene family |
| MGC31963 | Chromosome 1 open reading frame 85 |
| Hs.546395 | |

REFERENCES

Ambros, I. M., Ambros, P. F., Strehl, S., Kovar, H., Gadner, H., and Salzer-Kuntschik, M. (1991). MIC2 is a specific marker for Ewing's sarcoma and peripheral primitive neuroectodermal tumors. Evidence for a common histogenesis of Ewing's sarcoma and peripheral primitive neuroectodermal tumors from MIC2 expression and specific chromosome aberration. Cancer 67, 1886-1893.

Arvand, A., Bastians, H., Welford, S. M., Thompson, A. D., Ruderman, J. V., and Denny, C. T. (1998). EWS/FLI1 up regulates mE2-C, a cyclin-selective ubiquitin conjugating enzyme involved in cyclin B destruction. Oncogene 17, 2039-2045.

Arvand, A., Welford, S. M., Teitell, M. A., and Denny, C. T. (2001). The COOH-terminal domain of FLI-1 is necessary for full tumorigenesis and transcriptional modulation by EWS/FLI-1. Cancer Res 61, 5311-5317.

Bailly, R. A., Bosselut, R., Zucman, J., Cormier, F., Delattre, O., Roussel, M., Thomas, G., and Ghysdael, J. (1994). DNA-binding and transcriptional activation properties of the EWS-FLI-1 fusion protein resulting from the t(11;22) translocation in Ewing sarcoma. Mol Cell Biol 14, 3230-3241.

Baird, K., Davis, S., Antonescu, C. R., Harper, U. L., Walker, R. L., Chen, Y., Glatfelter, A. A., Duray, P. H., and Meltzer, P. S. (2005). Gene expression profiling of human sarcomas: insights into sarcoma biology. Cancer Res 65, 9226-9235.

Braun, B. S., Frieden, R., Lessnick, S. L., May, W. A., and Denny, C. T. (1995). Identification of target genes for the Ewing's sarcoma EWS/FLI fusion protein by representational difference analysis. Mol Cell Biol 15, 4623-4630.

Briscoe, J., Sussel, L., Serup, P., Hartigan-O'Connor, D., Jessell, T. M., Rubenstein, J. L., and Ericson, J. (1999).

Homeobox gene NRx2.2 and specification of neuronal identity by graded Sonic hedgehog signaling. Nature 398, 622-627.

Cavenzzana, A. O., Miser, J. S., Jefferson, J., and Triche, T. J. (1987). Experimental evidence for a neural origin of Ewing's sarcoma of bone. Am J Pathol 127, 507-518.

Choi, Y. L., Chi, J. G., and Suh, Y. L. (2001). CD99 immunoreactivity in ependymoma. Appl Immunohistochem Mol Morphol 9, 125-129.

Collini, P., Mezzelani, A., Modena, P., Dagrada, P., Tamborini, E., Luksch, R., Gronchi, A., Navarria, P., Sozzi, G., and Pilotti, S. (2003). Evidence of neural differentiation in a case of post-therapy primitive neuroectodermal tumor/Ewing sarcoma of bone. Am J Surg Pathol 27, 1161-1166.

Dauphinot, L., De Oliveira, C., Melot, T., Sevenet, N., Thomas, V., Weissman, B. E., and Delattre, O. (2001). Analysis of the expression of cell cycle regulators in Ewing cell lines: EWS-FLI-1 modulates p57KIP2 and c-Myc expression. Oncogene 20, 3258-3265.

Dellatre, O., Zucman, J., Plougastel, B., Desmaze, C., Melot, T., Peter, M., Heinrich, K., Houbert, I., de Jong, P., Rouleau, G., et al. (1992). Gene fusion with an ETS DNA-binding domain caused by chromosome translocation in human tumours. Nature 359, 162-165.

Deneen, B., and Denny, C. T. (2001). Loss of p16 pathways stabilizes EWS/FLI1 expression and complements EWS/FLI1 mediated transformation. Oncogene 20, 6731-6741.

Deneen, B., Hamidi, H., and Denny, C. T. (2003). Functional analysis of the EWS/ETS target gene uridine phosphorylase. Cancer Res 63, 4268-4274.

Dworzak, M. N., Fritsch, G., Buchinger, P., Fleischer, C., Printz, D., Zellner, A., Schollhammer, A., Steiner, G., Ambros, P. F., and Gadner, H. (1994). Flow cytometric assessment of human MIC2 expression in bone marrow, thymus, and peripheral blood. Blood 83, 415-425.

Fukuma, M., Okita, H., Hata, J., and Umezawa, A. (2003). Upregulation of ld2, an oncogenic helix-loop-helix protein, is mediated by the chimeric EWS/ets protein in Ewing sarcoma. Oncogene 22, 1-9.

Hahm, K. B., Cho, K., Lee, C., Im, Y. H., Chang, J., Choi, S. G., Sorensen, P. H., Thiele, C. J., and Kim, S. J. (1999). Repression of the gene encoding the TGF-beta type II receptor is a major target of the EWS-FLI1 oncoprotein. Nat Genet. 23, 222-227.

Hu-Lieskovan, S., Heidel, J. D., Bartlett, D. W., Davis, M. E., and Triche, T. J. (2005a). Sequence-specific knockdown of EWS-FLI1 by targeted, nonviral delivery of small interfering RNA inhibits tumor growth in a murine model of metastatic Ewing's sarcoma. Cancer Res 65, 8984-8992.

Hu-Lieskovan, S., Zhang, J., Wu, L., Shimada, H., Schofield, D. E., and Triche, T. J. (2005b). EWS-FLI1 fusion protein up-regulates critical genes in neural crest development and is responsible for the observed phenotype of Ewing's family of tumors. Cancer Res 65, 4633-4644.

Huppi, K., Martin, S. E., and Caplen, N. J. (2005). Defining and assaying RNAi in mammalian cells. Mol Cell 17, 1-10.

Jackson, A. L., Bartz, S. R., Schelter, J., Kobayashi, S. V., Burchard, J., Mao, M., Li, B., Cavet, G., and Linsley, P. S. (2003). Expression profiling reveals off-target gene regulation by RNAi. Nat Biotechnol 21, 635-637.

Jain, M., Arvanitis, C., Chu, K., Dewey, W., Leonhardt, E., Trinh, M., Sundberg, C. D., Bishop, J. M., and Felsher, D. W. (2002). Sustained loss of a neoplastic phenotype by brief inactivation of MYC. Science 297, 102-104.

Jaishankar, S., Zhang, J., Roussel, M. F., and Baker, S. J. (1999). Transforming activity of EWS/FLI is not strictly dependent upon DNA-binding activity. Oncogene 18, 5592-5597.

Khan, J., Wei, J. S., Ringner, M., Saal, L. H., Ladanyi, M., Westermann, F., Berthold, F., Schwab, M., Antonescu, C. R., Peterson, C., and Meltzer, P. S. (2001). Classification and diagnostic prediction of cancers using gene expression profiling and artificial neural networks. Nat Med 7, 673-679.

Kim, Y., and Nirenberg, M. (1989). *Drosophila* NK-homeobox genes. Proc Natl Acad Sci USA 86, 7716-7720.

Lessnick, S. L., Braun, B. S., Denny, C. T., and May, W. A. (1995). Multiple domains mediate transformation by the Ewing's sarcoma EWS/FLI-1 fusion gene. Oncogene 10, 423-431.

Lessnick, S. L., Dacwag, C. S., and Golub, T. R. (2002). The Ewing's sarcoma oncoprotein EWS/FLI induces a p53-dependent growth arrest in primary human fibroblasts. Cancer Cell 1, 393-401.

Masutomi, K., Yu, E. Y., Khurts, S., Ben-Porath, I., Currier, J. L., Metz, G. B., Brooks, M. W., Kaneko, S., Murakami, S., DeCaprio, J. A., et al. (2003). Telomerase maintains telomere structure in normal human cells. Cell 114, 241-253.

Matias-Guiu, X., Pons, C., and Prat, J. (1998). Mullerian inhibiting substance, alpha-inhibin, and CD99 expression in sex cord-stromal tumors and endometrioid ovarian carcinomas resembling sex cord-stromal tumors. Hum Pathol 29, 840-845.

May, W. A., Arvand, A., Thompson, A. D., Braun, B. S., Wright, M., and Denny, C. T. (1997). EWS/FLI1-induced manic fringe renders NIH 3T3 cells tumorigenic. Nat Genet. 17, 495-497.

May, W. A., Gishizky, M. L., Lessnick, S. L., Lunsford, L. B., Lewis, B. C., Delattre, 0., Zucman, J., Thomas, G., and Denny, C. T. (1993a). Ewing sarcoma 11;22 translocation produces a chimeric transcription factor that requires the DNA-binding domain encoded by FLI1 for transformation. Proc Natl Acad Sci USA 90, 5752-5756.

May, W. A., Lessnick, S. L., Braun, B. S., Klemsz, M., Lewis, B. C., Lunsford, L. B., Hromas, R., and Denny, C. T. (1993b). The Ewing's sarcoma EWS/FLI-1 fusion gene encodes a more potent transcriptional activator and is a more powerful transforming gene than FLI-1. Mol Cell Biol 13, 7393-7398.

McMahon, A. P. (2000). Neural patterning: the role of Nkx genes in the ventral spinal cord. Genes Dev 14, 2261-2264.

Mootha, V. K., Lindgren, C. M., Eriksson, K. F., Subramanian, A., Sihag, S., Lehar, J., Puigserver, P., Carlsson, E., Ridderstrale, M., Laurila, E., et al. (2003). PGC-1alpha-responsive genes involved in oxidative phosphorylation are coordinately downregulated in human diabetes. Nat Genet. 34, 267-273.

Mu, J., Skurat, A. V., and Roach, P. J. (1997). Glycogenin-2, a novel self-glucosylating protein involved in liver glycogen biosynthesis. J Biol Chem 272, 27589-27597.

Navas-Palacios, J. J., Aparicio-Duque, R., and Valdes, M. D. (1984). On the histogenesis of Ewing's sarcoma. An ultrastructural, immunohistochemical, and cytochemical study. Cancer 53, 1882-1901.

Price, M., Lazzaro, D., Pohl, T., Mattei, M. G., Ruther, U., Olivo, J. C., Duboule, D., and Di Lauro, R. (1992). Regional expression of the homeobox gene Nkx-2.2 in the developing mammalian forebrain. Neuron 8, 241-255.

Prieur, A., Tirode, F., Cohen, P., and Delattre, O. (2004). EWS/FLI-1 silencing and gene profiling of Ewing cells reveal downstream oncogenic pathways and a crucial role for repression of insulin-like growth factor binding protein 3. Mol Cell Biol 24, 7275-7283.

Qi, Y., Cai, J., Wu, Y., Wu, R., Lee, J., Fu, H., Rao, M., Sussel, L., Rubenstein, J., and Qiu, M. (2001). Control of oligodendrocyte differentiation by the NRx2.2 homeodomain transcription factor. Development 128, 2723-2733.

Rubin, J. B., Kung, A. L., Klein, R. S., Chan, J. A., Sun, Y., Schmidt, K., Kieran, M. W., Luster, A. D., and Segal, R. A. (2003). A small-molecule antagonist of CXCR4 inhibits intracranial growth of primary brain tumors. Proc Natl Acad Sci USA 100, 13513-13518.

Schenkel, A. R., Mamdouh, Z., Chen, X., Liebman, R. M., and Muller, W. A. (2002). CD99 plays a major role in the migration of monocytes through endothelial junctions. Nat Immunol 3, 143-150.

Smith, R, Owen L A, Trem D J, Wong J S, Whangbo J S, Golub T R, Lessnick S L. (May 2006). Expression profiling of EWS/FLI identifies NKX2.2 as a critical target gene in Ewing's sarcoma. Cancer Cell 9, 405-416.

Staege, M. S., Hutter, C., Neumann, I., Foja, S., Hattenhorst, U. E., Hansen, G., Afar, D., and Burdach, S. E. (2004). DNA microarrays reveal relationship of Ewing family tumors to both endothelial and fetal neural crest-derived cells and define novel targets. Cancer Res 64, 8213-8221.

Teitell, M. A., Thompson, A. D., Sorensen, P. H., Shimada, H., Triche, T. J., and Denny, C. T. (1999). EWS/ETS fusion genes induce epithelial and neuroectodermal differentiation in NIH 3T3 fibroblasts. Lab Invest 79, 1535-1543.

Thompson, A. D., Braun, B. S., Arvand, A., Stewart, S. D., May, W. A., Chen, E., Korenberg, J., and Denny, C. (1996). EAT-2 is a novel SH2 domain containing protein that is up regulated by Ewing's sarcoma EWS/FLI1 fusion gene. Oncogene 13, 2649-2658.

Thompson, A. D., Teitell, M. A., Arvand, A., and Denny, C. T. (1999). Divergent Ewing's sarcoma EWS/ETS fusions confer a common tumorigenic phenotype on NIH3T3 cells. Oncogene 18, 5506-5513.

Welford, S. M., Hebert, S. P., Deneen, B., Arvand, A., and Denny, C. T. (2001). DNA binding domain independent pathways are involved in EWS/FLI1 mediated oncogenesis. J Biol Chem 276, 41977-41984.

Zhang, H., Herbert, B. S., Pan, K. H., Shay, J. W., and Cohen, S, N. (2004). Disparate effects of telomere attrition on gene expression during replicative senescence of human mammary epithelial cells cultured under different conditions. Oncogene 23, 6193-6198.

Zwemer, J. P., and May, W. A. (2001). PDGF-C is an EWS/FLI induced transforming growth factor in Ewing family tumors. Oncogene 20, 626-633.

What is claimed is:

1. A method comprising: (a) detecting in a test sample of tumor cells from a patient having or suspected of having Ewing's sarcoma the expression of NKX2.2; and (b) comparing the expression of NKX2.2 in the test sample to the expression of NKX2.2 in a control sample of cells, wherein the expression of NKX2.2 in the test sample is higher than the expression of NKX2.2 in the control sample indicates cells of Ewing's sarcoma in the test sample.

2. The method of claim 1, wherein the expression of NKX2.2 is detected by measuring the amount of mRNA transcript of NKX2.2 present in the sample.

3. The method of claim 2, wherein measuring the amount of mRNA transcript of NKX2.2 present in the sample comprises amplifying the transcript of NKX2.2 by PCR and detecting the amplification products.

4. The method of claim 3, wherein measuring the amount of mRNA transcript of NKX2.2 present in the sample comprises microarray analysis.

5. A method comprising: (a) detecting in a test sample of tumor biopsy material from a patient having or suspected of having Ewing's sarcoma the expression of NKX2.2; and (b) comparing the expression of NKX2.2 in the test sample to the expression of N KX2.2 in a control sample of cells, wherein the expression of NKX2.2 in the test sample is higher than the expression of NKX2.2 in the control sample indicates cells of Ewing's sarcoma in the test sample.

6. The method of claim 5, wherein the expression of NKX2.2 is detected by measuring the amount of mRNA transcript of NKX2.2 present in the sample.

7. The method of claim 6, wherein measuring the amount of mRNA transcript of NKX2.2 comprises:

(a) amplifying the NKX2.2 transcript by PCR with at least one NKX2.2 specific primer to provide NKX2.2 amplification products; and
(b) observing the NKX2.2 amplification products.

8. The method of claim 6, wherein measuring the amount of mRNA transcript of NKX2.2 present in the sample comprises microarray analysis.

* * * * *

SEQUENCE LISTING

```
<160> NUMBER OF SEQ ID NOS: 14

<210> SEQ ID NO 1
<211> LENGTH: 2092
<212> TYPE: DNA
<213> ORGANISM: Homo sapiens

<400> SEQUENCE: 1
gcggccgccg gagcccgagc tgacgccgcc ttggcacccc tcctggagtt agaaactaag    60
gccggggccc gcggcgctcg gcgcgcaggc cgcccggctt cctgcgtcca tttccgcgtg   120
ctttcaaaga agacagagag aggcactggg ttgggcttca tttttttcct ccccatcccc   180
agtttctttc tcttttttaaa aataataatt atcccaataa ttaaagccaa ttccccctc    240 ccctccccca gtccctcccc ccaactcccc cctccccgc ccgccggggc aggggagcgc   300
cacgaattga ccaagtgaag ctacaacttt gcgacataaa ttttggggtc tcgaaccatg   360
tcgctgacca acacaaagac ggggttttcg gtcaaggaca tcttagacct gccggacacc   420
aacgatgagg agggctctgt ggccgaaggt ccggaggaag agaacgaggg gcccgagcca   480
gccaagaggg ccgggccgct ggggcagggc gccctggacg cggtgcagag cctgccctg    540 aagaacccct tctacgacag cagcgacaac ccgtacacgc gctggctggc cagcaccgag   600
ggccttcagt actccctgca cggtctggct gccggggcgc cccctcagga ctcaagctcc   660
aagtccccgg agccctcggc cgacgagtca ccggacaatg acaaggagac cccggcggc    720 gggggggacg ccggcaagaa gcgaaagcgg cgagtgcttt tctccaaggc gcagacctac   780
gagctggagc ggcgctttcg gcagcagcgg tacctgtcgg cgcccgagcg cgaacacctg   840
gccagcctca tccgcctcac gcccacgcag gtcaagatct ggttccagaa ccaccgctac   900
aagatgaagc gcgcccgggc cgagaaaggt atggaggtga cgccccctgcc ctcgccgcgc   960 cgggtggccg tgcccgtctt ggtcagggac ggcaaaccat gtcacgcgct caaagcccag  1020
gacctggcag ccgccacctt ccaggcgggc attcccttt ctgcctacag cgcgcagtcg  1080
```

```
ctgcagcaca tgcagtacaa cgcccagtac agctcggcca gcaccccca gtacccgaca    1140 gcacacccc tggtccaggc ccagcagtgg acttggtgag cgccgcccca acgagactcg    1200
cggccccagg cccaggcccc accccggcgg cggtggcggc gaggaggcct cggtccttat    1260
ggtggttatt attattatta taattattat tatggagtcg agttgactct cggctccact    1320
agggaggcgc cgggaggttg cctgcgtctc cttggagtgg cagattccac ccacccagct    1380
ctgcccatgc ctctccttct gaaccttggg agagggctga actctacgcc gtgtttacag    1440
aatgtttgcg cagcttcgct tctttgcctc tccccggggg gaccaaaccg tcccagcgtt    1500
aatgtcgtca cttgaaaacg agaaaaagac cgacccccca ccctgctttt cgtgcatttt    1560
gtaaaatatg tttgtgtgag tagcgatatt gtcagccgtc ttctaaagca agtggagaac    1620
actttaaaaa tacagagaat ttcttccttt ttttaaaaaa aaataagaaa atgctaaata    1680
tttatggcca tgtaaacgtt ctgacaactg gtggcagatt tcgcttttcg ttgtaaatat    1740
cggtggtgat tgttgccaaa atgaccttca ggaccggcct gtttcccgtc tgggtccaac    1800
tcctttcttt gtggcttgtt tgggtttgtt ttttgttttg ttttgttttt tgcgttttcc    1860
cctgctttct tcctttctct ttttatttta ttgtgcaaac atttctcaaa tatggaaaag    1920
aaaaccctgt aggcagggag ccctctgccc tgtcctccgg gccttcagcc ccgaacttgg    1980
agctcagcta ttcggcgcgg ttccccaaca gcgccgggcg cagaaagctt tcgattttttt    2040 aaataagaat tttaataaaa atcctgtgtt taaaaaagaa aaaagaaaaa aa    2092

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatccccata gaggtgggaa gcttatttca agagaataag cttcccacct ctattttttg    60
gaac                                                                 64

<210> SEQ ID NO 3
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgagttcca aaaatagag gtgggaagct tattctcttg aaataagctt cccacctcta    60
tggg                                                                 64

<210> SEQ ID NO 4
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatccccgac gccaagggca ttgcagttca agagactgca atgcccttgg cgtcttttttg    60 gaac                                                                 64
```

```
<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcgagttcca aaaagacgcc aagggcattg cagtctcttg aactgcaatg cccttggcgt      60
cggg                                                                  64

<210> SEQ ID NO 6
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatccccctt acgctgagta cttcgattca agagatcgaa gtactcagcg taagttttg       60 gaac                                                                  64

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatccccgac tcttgggagg gagttattca agataact ccctcccaag agtcttttg         60 gaaac                                                                 65

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcgagttcca aaaagactct tgggagggag ttatctcttg aataactccc tcccaagagt      60
cggg                                                                  64

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccggccatgc ctctccttct gaattcaaga gattcagaag gagaggcatg gtttttg        57

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 10
aattcaaaaa ccatgcctct ccttctgaat ctcttgaatt cagaaggaga ggcatgg        57

<210> SEQ ID NO 11
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcgagttcca aaacttacg ctgagtactt cgatctcttg aatcgaagta ctcagcgtaa       60
gggg                                                                   64

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccatgcctct ccttctgaa                                                   19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctacgacagc agcgacaacc                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccttggaga aaagcactcg                                                  20
```